US007740612B2

(12) United States Patent
Hochman

(10) Patent No.: US 7,740,612 B2
(45) Date of Patent: Jun. 22, 2010

(54) SELF-ADMINISTRATION INJECTION SYSTEM

(75) Inventor: Mark N. Hochman, Great Neck, NY (US)

(73) Assignee: Milestone Scientific, Inc, Livingston, NJ (US)

( * ) Notice: Subject to any disclaimer, the term of this patent is extended or adjusted under 35 U.S.C. 154(b) by 126 days.

(21) Appl. No.: 12/107,160

(22) Filed: Apr. 22, 2008

(65) Prior Publication Data

US 2009/0030366 A1    Jan. 29, 2009

Related U.S. Application Data

(60) Provisional application No. 60/952,489, filed on Jul. 27, 2007.

(51) Int. Cl.
*A61M 1/00* (2006.01)

(52) U.S. Cl. .................. 604/121; 604/118; 604/30; 604/31; 604/246; 604/67

(58) Field of Classification Search ............ 604/28, 604/48, 504, 151, 152, 154, 155, 272, 31, 604/65, 67, 121
See application file for complete search history.

(56) References Cited

U.S. PATENT DOCUMENTS

| | | | |
|---|---|---|---|
| 5,180,371 A | 1/1993 | Spinello |
| 5,643,218 A | 7/1997 | Lynn |
| 6,019,745 A | 2/2000 | Gray |
| D422,361 S | 4/2000 | Herbst et al. |
| D423,665 S | 4/2000 | Herbst et al. |
| D427,314 S | 6/2000 | Herbst et al. |
| 6,132,414 A | 10/2000 | Herbst et al. |
| 6,152,734 A | 11/2000 | Herbst et al. |
| 6,200,289 B1 | 3/2001 | Hochman et al. |
| 6,269,340 B1 | 7/2001 | Ford |
| 6,652,482 B2 | 11/2003 | Hochman |
| 6,788,885 B2 | 9/2004 | Mitsunaga et al. |
| 6,887,216 B2 | 5/2005 | Hochman et al. |
| 6,945,954 B2 | 9/2005 | Hochman et al. |

(Continued)

FOREIGN PATENT DOCUMENTS

WO     WO 2005/077441     8/2005

(Continued)

OTHER PUBLICATIONS

International Search Report for PCT application PCT/US2008/071114.

(Continued)

*Primary Examiner*—Nicholas D Lucchesi
*Assistant Examiner*—Leah Stohr

(57) ABSTRACT

Self-injection system allows a user to inject a drug from a cartridge carrying unique identification information, into any one of a plurality of injection sites. Tissue at each injection site is associated with at least one injection parameter, such as flow-rate, that is different for each site. A scanner reads the identification information of the cartridge and cooperates with a central processing unit to determine the validity of the drug in order to permit an injection procedure to commence. The central processing unit has a memory for storing the different injection parameters and controls a drive unit for driving fluid from the cartridge and through a needle into the selected tissue, at the injection parameter that is associated with the user selected tissue for the injection.

18 Claims, 13 Drawing Sheets

U.S. PATENT DOCUMENTS

| | | | |
|---|---|---|---|
| 7,264,148 | B2 | 9/2007 | Tachibana |
| 2002/0052574 | A1* | 5/2002 | Hochman et al. ............. 604/31 |
| 2003/0233069 | A1* | 12/2003 | Gillespie et al. ............ 604/131 |
| 2005/0004514 | A1 | 1/2005 | Hochman |
| 2005/0029277 | A1* | 2/2005 | Tachibana ..................... 221/9 |
| 2005/0143864 | A1* | 6/2005 | Blomquist ................. 700/282 |
| 2006/0102174 | A1 | 5/2006 | Hochman |
| 2006/0122555 | A1 | 6/2006 | Hochman |

FOREIGN PATENT DOCUMENTS

| | | |
|---|---|---|
| WO | WO 2007/088444 | 8/2007 |

OTHER PUBLICATIONS

Written Opinion of the International Searching Authority for PCT application PCT/US2008/071114.

Hochman, Mark N., et al., Interstitial Tissue Pressure Associated With Dental Injections: A Clinical Study, Quintessence International, vol. 37, No. 6, Jun. 2006, pp. 469-476.

U.S. Appl. No. 11/614,471, filed Dec. 21, 2006, M. Hochman.

Written Opinion of the International Searching Authority of International Application No. PCT/US2008/071114.

* cited by examiner

SELF-ADMINISTRATION INJECTION SYSTEM

CROSS-REFERENCE TO RELATED APPLICATIONS

This application claims priority on U.S. Provisional Application Ser. No. 60/952,489 entitle "Compliance Injection System for In-Home Self-Administration Device" filed Jul. 27, 2007, which is incorporated here by reference.

FIELD AND BACKGROUND OF THE INVENTION

The present invention relates generally to the field of medicament delivery systems and in particular to a drug deliver platform comprising an injection device for delivering medicaments to a subject through a needle. More specifically, the present invention relates to a drug delivery platform for self-administration of an injection having one or more of a medicament delivery device with stored tissue and site specific parameters for different injections, a non-sequential user feedback control process, a training component, a failsafe component, a drug monitoring and reporting component, a compliance assistance component, and a dynamic diagnostic drug delivery component. Further, this application relates to a method for using the same.

Human error in the health care environment accounts for an estimated 98,000 deaths a year. This staggering figure exceeds the numbers of death related to automobile accidents (about 43,450), breast cancer (42,300) or AIDS (16,500) as reported by the National Academy of Science [1]. National outcry has mandated that improved systems be developed to reduce the number of mistakes made in the health care setting. There is, therefore, an unaddressed, long felt need for a means of improving patient compliance by way of training, tracking and verifying subcutaneous injections performed on patients in an outpatient setting.

A "Standard of Care" in drug administration is defined by the ability to control a variety of drug delivery parameters of the injection/infusion event and ultimately ensure patient safety and patient comfort. These elements are currently lacking as it pertains to in-home, self-administered injection devices. Such devices may be generally categorized into two groups: manual disposable syringe based devices or auto-injection "pen" devices.

Manual disposable syringe based devices have existing since the mid-1800's. In 1844, Irish physician Francis Rynd, invented the hollow needle. In 1853, two physicians, Scottish physician Alexander Wood and the French physician Charles Pravaz, independently developed first practical hypodermic syringes [2]. Companies such as Becton Dickinson (1 Becton Drive, Franklin Lakes, N.J. 07417) have developed disposable syringe based devices for over 100 years. These devices were designed for a single purpose of performing a subcutaneous injection through a hollow-bore needle affixed to the syringe device. Syringes are simple mechanical systems with no capability of refined fluid dynamics or ability to integrate advanced digital capabilities.

Auto-injection "pen" devices have recently become increasingly popular for single-dose or multi-dose, at-home self-administration. These auto-injection "pen" devices are primarily designed to accomplish two basic objectives: convenience and automation of drug delivery in an outpatient setting. These are typically mechanically spring-loaded devices that advance a plunger or rubber stopper to transfer medication via a hollow-bore needle to a patient's tissues. Auto-injection "pen" devices lack the ability to regulate flow-rate of injection, tissue exit-pressure of the injection or to integrate advanced digital capabilities. A significant limitation of auto-injection pens are the inability to control injection parameters such as flow-rate and pressure, or to collect and transfer digital information from the device to other sources.

See published international patent applications WO 2005/077441 A2 and WO 2007/088444 A1, applied for by Ares Trading S. A., which disclose hand-held electronically controlled injection devices designed to perform an injection by first mechanically advancing the needle into the subject's tissue, and then advancing a plugger for injecting the liquid drug into the tissue. The initial, and potentially most uncomfortable needle insertion step is performed by the device as part of its automated function, rather than by the subject. The speed of insertion of the needle is set by the device and automation of the insertion step may contribute to further discomfort, in that the subject may feel as though he or she has, in effect, been stabbed by the device, in a manner over which the subject has no control.

Manual syringes and auto-injection "pen" devices are devices that are designed to conveniently administer a fluid-flowing drug subcutaneously via a hollow-core needle. These devices are not designed to reduce apprehension, pain, user pain perception and/or prevent local trauma during the delivery of the medication. The inability to precisely control flow-rate and/or exit-pressure of the drug, and, in the devices that automate the insertion step, the inability to control needle insertion, further increase the chance of a negative experience by the home user, possibly leading to a reduction in home-use compliance when using such devices.

The mechanical design of these devices incorporates mechanical limitations that result in ineffective management of fluid flow specifically, and the overall inject process in general.

Another major deficiency in state of the art injection devices is that they do not provide a means for promoting user compliance for the outpatient, self-injecting segment of the market. Current manual syringes and auto-injection "pen" devices are susceptible to operator error and, as a result, lower user compliance. These operator mistakes can unfortunately lead to patient deaths and iatrogenic illnesses. There is, therefore, an unaddressed and long felt need to provide an apparatus and method for improving the safety of self-administration of medicaments, as well and improving patient drug regimen compliance.

SUMMARY OF THE INVENTION

It is an object of the present invention to provide a multiple or single unit drug delivery platform designed to meet the above-identified and other requirements by providing less threatening means to accurately control injection parameters of insertion, flow-rate and/or exit-pressure and to verify the amount of a drug administered as well as the flow-rate and/or exit-pressure at which it was administered during the administration of a self-injected, in-home subcutaneous drug administration.

A further object of the present invention is to provide means to verify that the drug used is valid, which is to say any one or more of: authentic (non-counterfeit); unadulterated; viable (within its date of expiration); and in proper condition for application (e.g., at the optimal temperature for application).

Another object of this present invention is to provide a means to have specific injection parameters (flow-rate and/or exit-pressure, time and volume) that is/are unique for a specific anatomical location of the body to receive said injection. Presenting these injection profiles to allow the user to select the unique site-specific injection profile to be used for each application.

Yet another object of the present invention is to provide means to generate a digital treatment record of the actual drug administration procedure recorded during a self-administered, subcutaneous or other type of injection, including an integrated calendar, time-stamp and time-clock to document when an injection has occurred and provide for an alarm and/or reminder as to when a future injection should be performed as prescribed by the treating doctor.

Further, it is an object of this invention to provide a verification system to determine and document proper dosage and drug regimen at the time of administration, including cross-referencing patient histories and medical records for adverse drug interactions and allergies.

Further still, it is an object of this invention to provide means to the subject or patient for identifying the proper site of the drug by presenting an interactive learning and teaching experience that is integrated within the drug delivery system to encourage usage, promote safe application and improve patient compliance.

Another object of this invention is to provide a subject with means to define specific parameters of flow-rate and exit-pressure and to store these parameters in a User Specific Injection Profile that is customized to individual patient preferences and requirements.

Accordingly, a self-administered medicament deliver system is described herein various embodiments of the invention are designed to improve patient compliance; facilitate safety through training, coaching and schedule maintenance; track and verify treatment regimens; provide critical failsafe check points; enable a digital data record of treatment information; enable encrypted data transfer with remote computer systems; and allow for personalized self-medication in a non-threatening manner.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

The present invention comprises to a self-administration injection device or drug delivery platform comprising: a medicament delivery device with tissue and site specific parameters for injection; a non-sequential user feedback control process; a training component; a failsafe component; a drug monitoring and reporting component; a compliance assistance component; and a dynamic diagnostic drug delivery component.

The term "medicament" as used in describing the various embodiments of this invention includes an injectable liquid medicine, medication, drug, pharmaceutical, prescriptive, agent, antidote, anti-venom, hormone, stimulant, vasodilator, anesthetic, nutritional supplement, vitamin and/or mineral compound, saline solution, biological, organic compound, genetically and/or chemically modified protein and/or nucleic acids, or other liquid that is adapted to be injected into the tissue of a subject.

Medicament Delivery System

Embodiments of this invention include the novel incorporation of a variety of single and multiple unit injection devices as part of an integrated system designed to deliver medicaments in a virtually painless and non-threatening manner. Specifically disclosed are designs of the invention which include some components that are remotely located from one another on the drug delivery platform as described in detail below.

Figure 1:
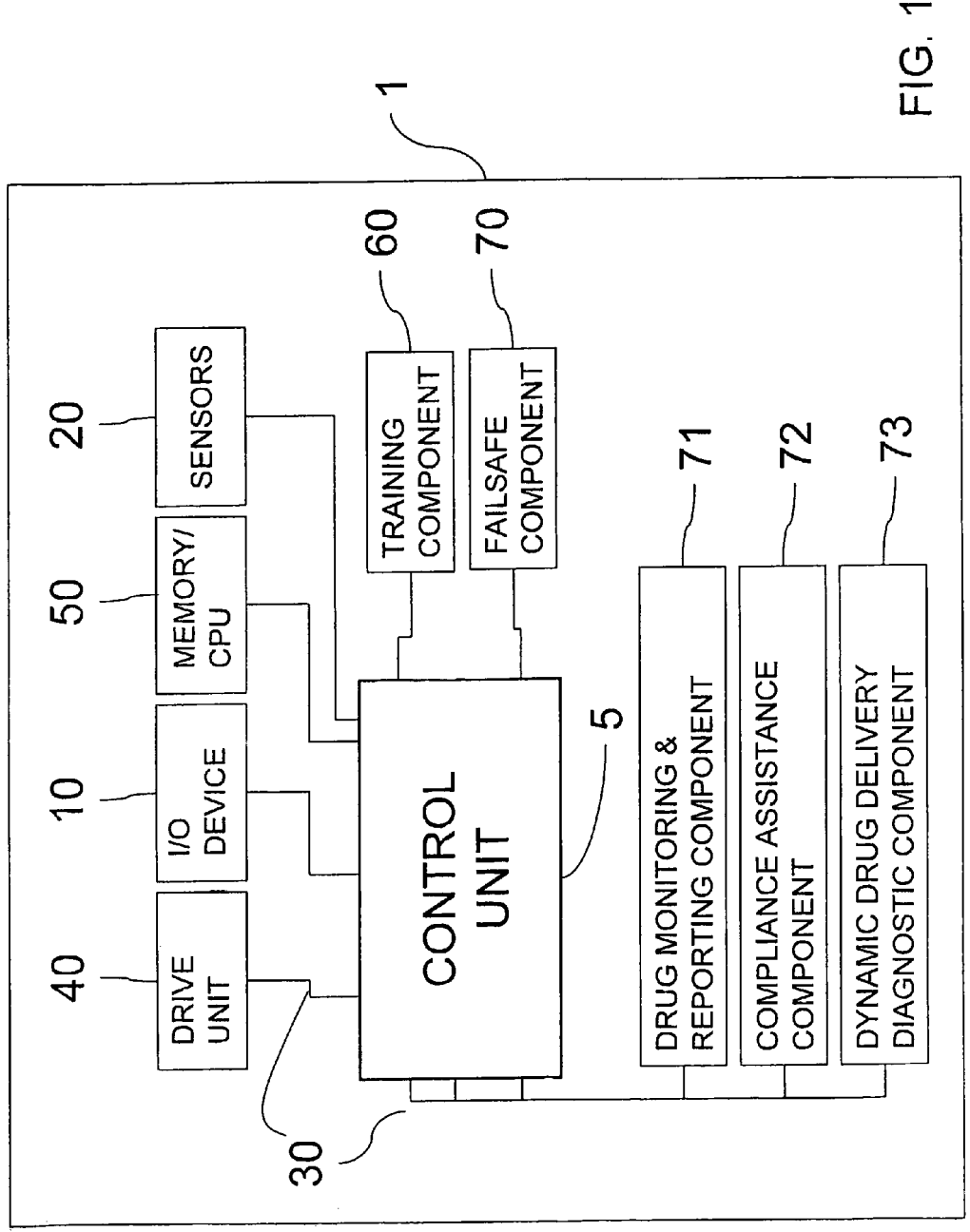
FIG. 1 is a schematic diagram of the self-administration injection system with subcomponents, of the present invention.

With reference to FIG. 1, the self-administration injection delivery platform 1 (the delivery platform) comprises a control unit 5 that receives data and instructions from the user or subject (not shown) via an I/O device(s) 10 and the environment through various sensor means 20, over an electronic circuit 30. The control unit 5 further supplies control signals for a drive unit 40 as well as data and information to the I/O device(s) 10, according to a program stored in a CPU/memory component 50. The memory component runs various routines, tasks, algorithms, and programs that integrate delivery system subcomponents; namely: a training component 60; a failsafe component 70; a drug monitoring and reporting component 71; a compliance assistance component 72; and a dynamic drug delivery diagnostic component 73; these subcomponents being described in more detail below. The synergistic effect of these collaborating subcomponents is to create a interactive, user-feedback capable, medicament delivery system, capable of producing virtually painless medicament administration and concomitant patient comfort and regimen compliance.

Figure 2:
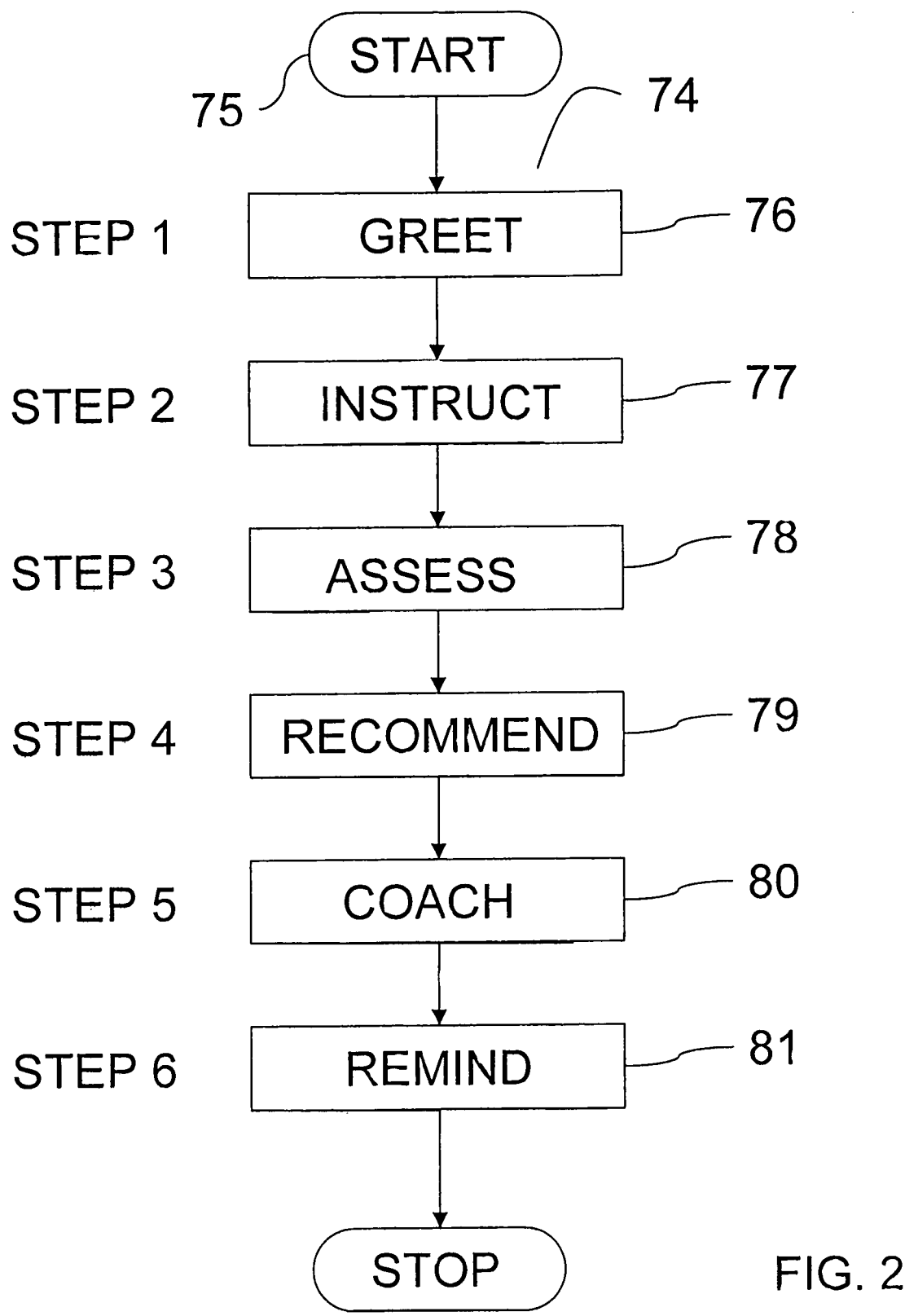
FIG. 2 is a flow chart of a linear automated process embodiment of the invention.

In certain embodiments of the invention, the delivery system is fully automated and follows a sequence of routines coordinated by the control unit 5 and designed to safely, effectively and comfortably administer the medicament by a self-administered injection. FIG. 2 illustrates the typical steps certain embodiments of the invention would take when operating automatically and linearly. The linear, automated process 74 of FIG. 2 begins with system initiation or a START step 75 leading immediately to the first step 1 of greeting the user or subject at 76. The system in this example, is configured to automatically proceed to a second step 2 at 77 of the process, by beginning to instruct the user on proper medicament administration and protocols. After completing the instruction step 77 the system 1 of FIG. 1, automatically begins the third step 3 of assessment at 78. During step 3, the system 1 will automatically process the user's medical record in preparation of making a recommendation 79 in the following step 4. During step 4, the system 1 notifies the user of its recommendation 79 as far as a course of action, allowing the user to begin making the necessary preparations to receive administration of the medicament by self-administered injection. After make it's recommendation 79, the system is ready to begin administration of medicament at which point it will enter step 5 of the process at 80 wherein it will coach the user in real-time as to how to perform the injection and the status of the same. After completing the procedure, the system 1 will automatically begin its review and remind process as part of step 6. During this step 6 it will perform a number of administrative functions, including reminding the user at 81 of the next administration date and time. The system 1 will then shut down the process 74 completing, as indicated at the step called STOP.

Also disclosed, however, is a system that integrates the user into adjusting the administration procedure so that it does not necessarily follow a linear sequence of routines.

Figure 3:
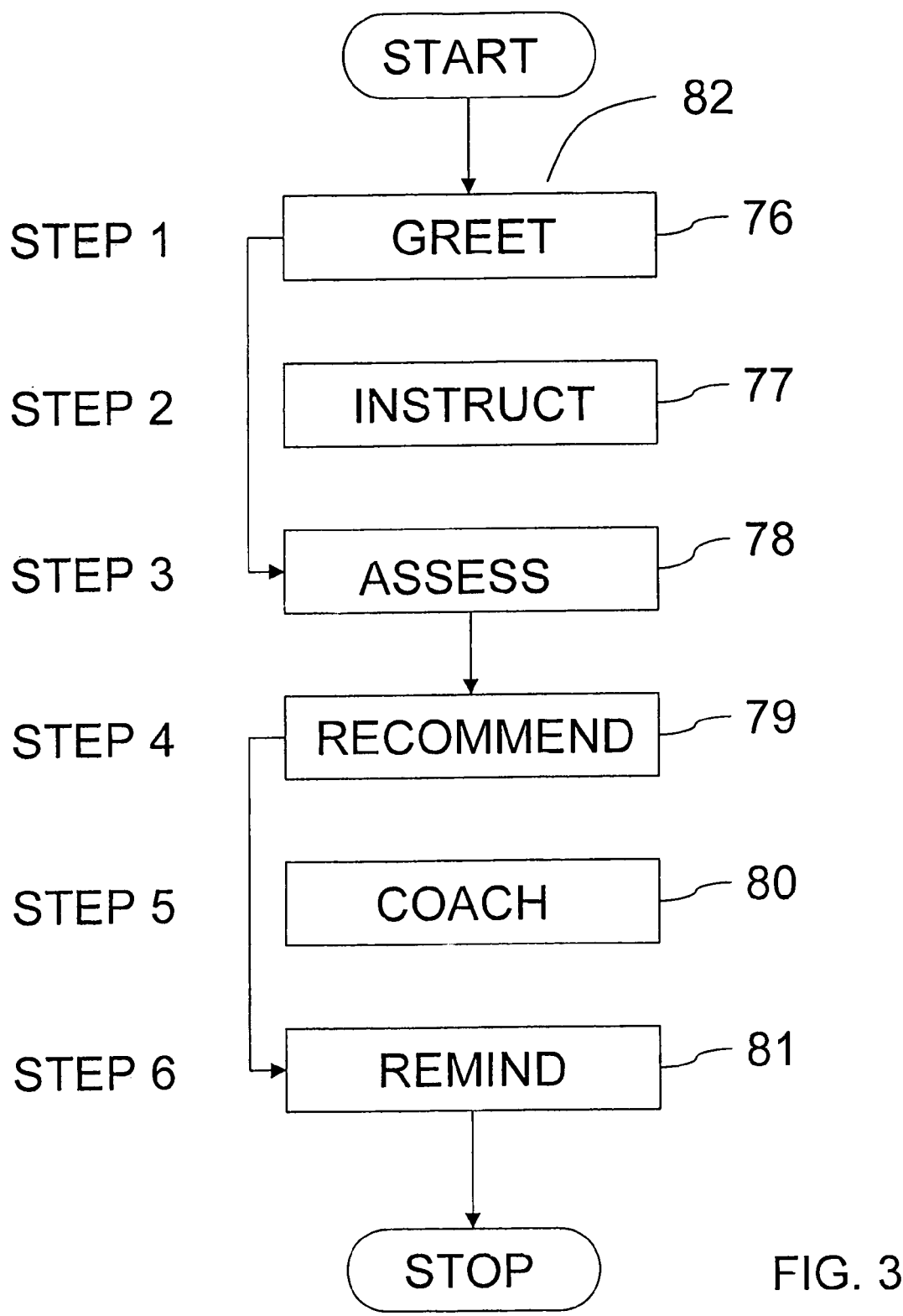
FIG. 3 is a flow chart of a leap-frog process embodiment of the invention.

For instance, instead of executing steps START, 1 to 6, STOP of the medicament administration protocol of FIG. 2, the delivery system may be adjusted so that it executes only steps START and 1 to 3. By way of example, in FIG. 3 the same steps 1 to 6 of FIG. 2 are present, however in this non-sequential, leap-frog process 82 the system 1 is configured to skip the instruction step 77 and go from the greeting 76 straight to the assessment 78. Having skipped to step 3 from step 1, the process 82 will automatically begin step 4, and recommend 79, a course of action to the user at which point it will skip step 5 (coaching 80), and proceed immediately to administering the medicament (not shown), to remind 81 the user of the next scheduled event and to STOP.

Figure 4:
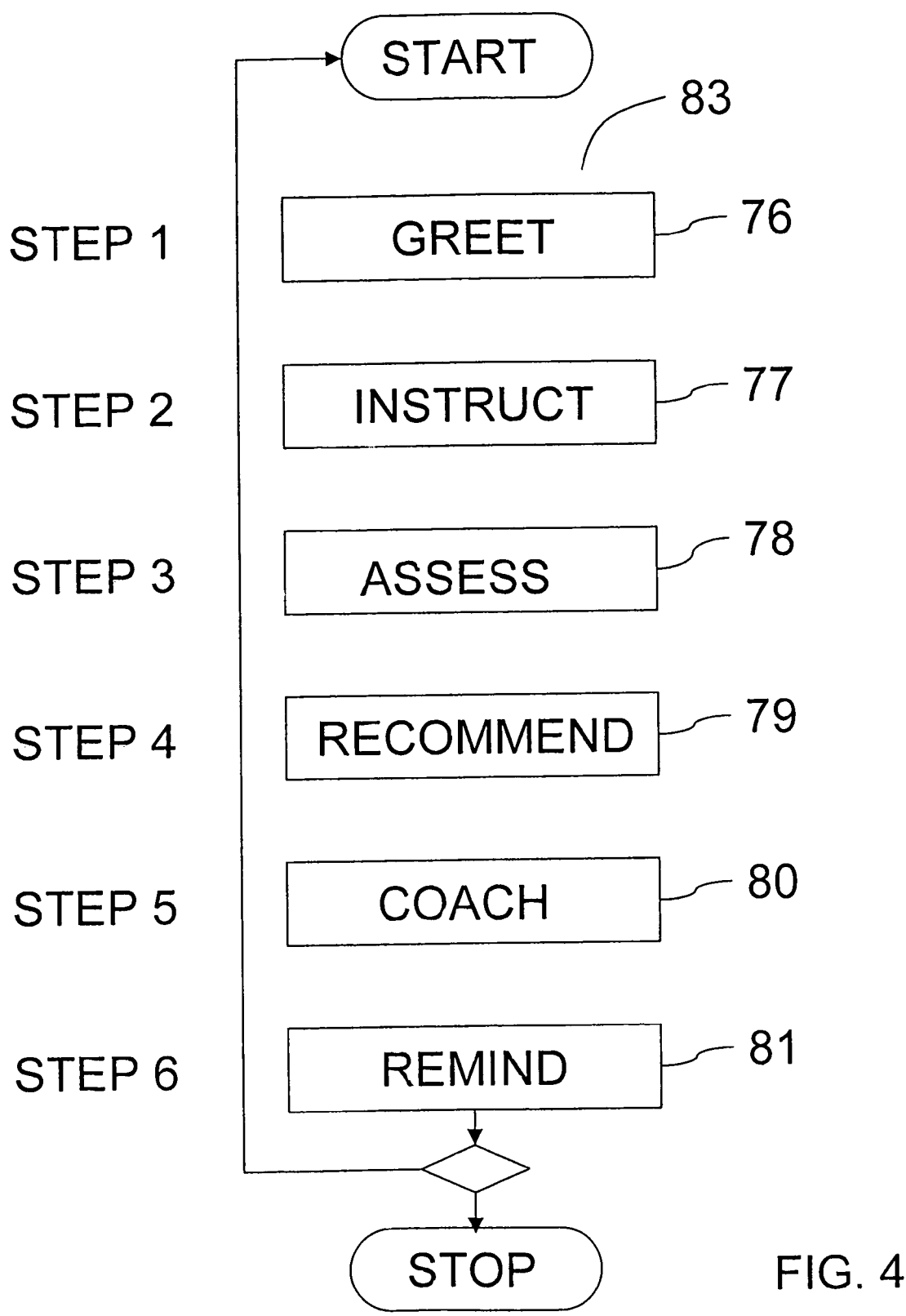
FIG. 4 is a flow chart of a reverse process embodiment of the invention.

By way of a further example, the delivery system 1 could be adjusted by the user to perform the steps out of sequential order, in reverse order, or in some combination thereof. FIG. 4 illustrated an example of a reverse order process 83. Unlike process 74 or 82, process 83 begins at step 6, remaining resident in the system's memory to periodically remind 81 the user of upcoming or missed medicament events. The user has the option of terminating process 83 by going directly to STOP, or to respond to the reminder 81 and allow the system 1 to initialize at START.

Therefore, what is also disclosed as certain embodiments of the invention is an optional, semi-automatic procedure requiring the user to be interactive by controlling at least one of the specific steps of the medicament delivery protocol while allowing the delivery system and platform to automate the remaining steps. The system thus gives the user a new degree of control over the process that was not previously available. Further, such a system allows a user to customize his or her experience by adjusting certain parameters of the administration protocol to what is appropriate to each user's age, experience, pain threshold, physiology, physical condition and environment. This degree of control is attained through an electronic controller means such as, for instance, a programmable logic controller (PLC) embedded in the delivery system, and allows the user to ultimately control aspects of the process of injection through input means, while still receiving instructions and data and while under the control of the system for other aspects of the injection. The process is further modulated in real-time by receiving interactive feedback from the user in response to the information provided by the delivery system through output means to the user.

Some of the medicament administration parameters that are customizable by the user via the electronic controller are the tissue type and injection site specific parameters for injection. The user is able to select where on his or her body and into what tissue he or she wishes to receive the injection of medicament, after receiving initial guidance from the delivery system as described in more detail below. For example, if the user is scheduled to receive one injection per day of a drug, and may make that injection in an arm, in a thigh or in the abdomen, and the user wishes to administer the injection in an arm on one day, in a thigh on the next day, and in the abdomen on the third, the system of the invention empowers the user make the selection of injection site. Upon receiving that selection via the input means, the system then selects the appropriate parameters, e.g. of flow rate and/or pressure for that injection site, as perhaps modified further by values that take the users person sensitivity into account as well. This degree of selection but with control over the required parameters is unique in the art, adding to overall user comfort level, standard of care and, ultimately, user compliance.

Medicament Delivery Platform

Referring now again to the drawings in which like reference numerals are used to refer to the same or functionally similar elements:

Example 1

Figure 5:
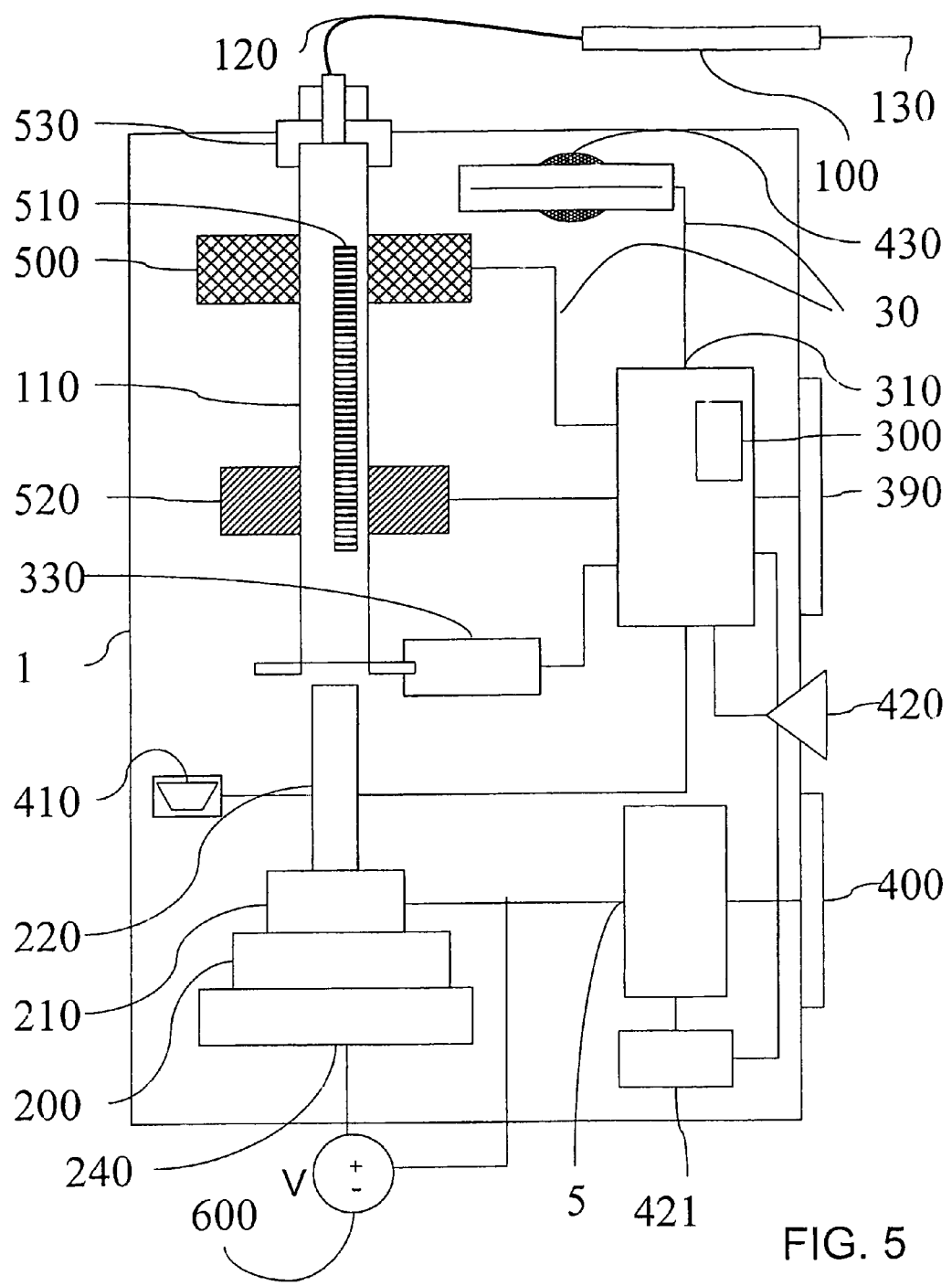
FIG. 5 is a schematic plan view of a self-administration injection device in accordance with an embodiment of the invention.

FIG. 5 discloses a multiple unit, computer-controlled medicament deliver platform 1 utilizing a separate handpiece component 100. The deliver platform 1 may utilize a fixed flow-rate or variety of flow-rates that are programmed within a digital memory 300 associated with a central processing unit 310. The system may also elect to control and monitor exit-pressure as a parameter of the injection (as discussed in more detail below).

U.S. Pat. No. 6,200,289, which was co-invented by the inventor of the subject application; its related U.S. Pat. Nos. 6,788,885; 6,945,954; and 6,887,216; as well as its related U.S. Published Patent Applications 2005/0004514; 2006/0102174; and 2006/0122555; which are all incorporated herein by reference in their entirety; disclose devices that control the flow rate and/or the exit pressure for a fluid being injected into a patient.

The handpiece 100, which is preferably disposable, and other aspects of the overall medicament delivery platform 1 for administering medicaments in a controlled manner with reduced pain to the subject are disclosed in U.S. Pat. Nos. 5,180,371; D422,361; D423,665; D427,314; 6,132,414; 6,152,734; 6,652,482; and U.S. patent application Ser. No.

11/614,471 filed Apr. 19, 2007; all of which are incorporated herein by reference in their entirety.

The delivery platform 1 is partly controlled via a touch-screen LCD 390 located on the outside of the unit where it is easily viewed and used as input means by the subject (not shown), during the various steps on a self-administered injection process according to the invention. It is also possible to utilize a wireless or hardwired foot pedal or control (not shown) integrated with a control activator unit 400 to function as a rheostatic controller for variable current control or as a switch that functions as a start and stop controller for the system.

In one embodiment of the invention, the handpiece 100 is made up of four basic elements: (1) a cartridge holder or vessel connection component 110; (2) microtubing 120 interposed between the drug source in cartridge 110 and a hand-held part or section of the handpiece 100 that is meant to be held in the user's hand like a pencil; (3) hand-held part or section itself that is ergonomically designed to increase user dexterity and accuracy of use; and (4) a needle 130 affixed to the hand-held part or section or the handpiece 100. It is conceivable that this handpiece component could be designed as a re-usable device for in-home self-injection. It is also conceivable that the design of the handpiece system could allow the medicament to be placed between the needle 130 and the microtubing 120 in which case, the delivery platform 1 would perform a hydraulic function via the microtubing 120 section to the medication adjacent to the needle 130. The hydraulic operation of the handpiece 100 would be accomplished through the use of a rubber stopper or similar interposing material placed between the medicament and the hydraulic fluid to be able to force the medicament through the hollow-bore needle 130 into the patient tissues.

The delivery platform 1 is equipped with a motor assembly 200 equipped with a pressure sensor 210. Motor assembly 200 functions to move a plunger 220 into and out from the syringe or cartridge 110. The pressure sensor 210 monitors the various forces exerted by the motor assembly 200 transmitted via the plunger 220 and sends the force data to the control unit 5. The control unit 5, in turn coordinates the motor assembly 200 activity with the user input received from the activator unit 400 or other I/O device, for example, in the form of the touch screen 390 of other I/O device 10 in FIG. 1. The electronic signals received from the control unit 5 are translated by an electrical motor control circuit 240.

The electronic circuit system of the delivery platform 1 includes the central processing unit 310 operatively coupled to the digital or mechanical memory device 300. The memory 300 can be configured to store processor-readable code instructing the processor 310 to perform the functions described above. In some embodiments, the processor-readable code can be modified and/or updated as circumstances dictate (as described in further detail below). The electronic circuit system also operates to receive electronic signals from a switch 330 which may be in the form of a proximity sensor and/or the start button. The switch 330 operates to initialize and terminate the system processes and is electronically integrated with device the various I/O devices of the delivery platform 1, as, for instance, visual output devices, such as the LCD 390 or peripheral display devices connected through at least one hardware interface or connector 410. In some embodiments of the invention an audio input/output device such as a speaker 420 is also integrated into the electronic circuit system and can be driven, for example, by an enunciator 421 that can cause speaker 420 to give the user verbal information and/or instructions.

Some embodiments may include at least one hardware interface 410 comprising a network interface configured to couple the delivery platform 1 to a communications network such as the Internet or other global computer network, an intranet, a local area networks (LANs), a Personal Area Networks (PANs), BLUETOOTH (™) (Bluetooth SIG, Inc.; 500 108th Avenue NE, Suite 250, Bellevue, Wash. 98004) or other wireless protocol device, Wide Area Networks (WANs), Virtual Private Networks (VPNs) and the like. Such an arrangement can be used, for example, to download replacement processor readable code from a central network to the memory device 300. The delivery platform my, in this way, be configured to transmit and receive electronic data to various receivers (not shown) such as, for instance, a centralized network, a home computer, a mobile computing platform, etc. Hardwire transfer via standardized or proprietary means, i.e. universal serial bus (USB), FIREWIRE (™) (Apple, Inc.; 1 Infinite Loop Cupertino, Calif. 95014) or other proprietary connection, and IEEE 1394 standard interfaces, etc. is also envisaged in this embodiment with connectivity through at least one hardware interface 410. Still further, by way of example, the network interface may also include a telephone, cellular phone, cellular modem, telephone data modem, fax modem, wireless transceiver, ethernet card, cable modem, digital subscriber line interface, bridge, hub, router, or other similar device.

The memory device 300 can include one or more types of memory. For example, the memory device can include a read only memory (ROM) component and a random access memory (RAM) component. The memory device can also include other types of memory suitable for storing data in a form retrievable by the microprocessor, for example, electronically-programmable read only memory (EPROM), erasable electronically-programmable read only memory (EEPROM), or flash memory. Further, the term "memory device" or simply "memory" as used in describing the various embodiments of the present invention also includes any apparatus capable of storing analog or digital information, such as instructions and/or data as, for instance, non-volatile memory, volatile memory, magnetic media, optical media, compact disks (CDs), digital versatile disks (DVDs), and/or a Redundant Arrays of Independent Disks (RAID) array, etc.

The delivery platform 1 may also have a port 430 capable of accepting digital media such as a "smart card", or similar portable digital storage solutions. The function of this removable digital media is described in more detail below, e.g. as a drug monitoring and reporting component of the invention.

The smart card is a physical, portable, electronic mechanism designed to store the essential elements of a subject's medical history so it can be readily accessed and updated by medical personnel via laptop or hand-held computers when real-time connectivity to a database is unavailable. The smart card allows data capture and delivery of medical records information including x-rays, MRIs, EKGs, or text to enable more effective health support and more efficient management of medical information management in a mobile society. The smart card would work with a computer-based patient record (CPR). Data is stored on the smart card, in the CPR database, and when there is connectivity (Wireless LAN, Radio, etc.) the data is also stored in a central database server. The smart card is a small device, the same size as a dog tag, with a storage capacity in the range of at least 8 to 128 megabytes and preferably more. In certain embodiments it may be a rugged, low power consumption, flash memory device that is hardware and operating system independent. In addition, the primary interface is a PC Card port adapter, compatible with any PCMCIA (Personal Computer Memory Card International Association) Type II enabled device. An alternate means is via a standard external parallel and/or USB (Universal Serial Bus) drive which may also be interfaced with at the at least one hardware interfaces 410.

In some embodiments of the delivery platform, the device is capable of uniquely recognizing the drug to be used within the unit. This could be accomplished as, for instance, with bar code scanner 500 reading unique identifying information from a bar code 510 affixed to the cartridge 110 containing the medicament. The purpose and function of such technology as well as a description of acceptable technological alternatives is described in more detail below e.g. as the failsafe component of the invention.

In this example, the embodiment of the invention has one or more integrated speakers 420 and displays 390, LED's (not shown) and switches 330, 400. In the preferred embodiment the Touch Screen LCD 390 would be provide for input commands as well as display information. This display could also serve to allow digital video's to be displayed for teaching and training purposes, as described in further detail below, e.g. the training component of the invention.

Another feature of this embodiment of delivery platform 1 is an internal thermal warming element 520 to warm the temperature of the drug placed therein with means to externally measure the temperature of the drug vessel. The drug chamber to which the drug vessel is placed within would have the capability to detect the temperature of the drug indirectly through a thermal coupling sensor for example in unit 520, or within a cartridge adaptor 530 of the delivery platform 1.

The delivery platform 1 has a power source or power supply 600 of rechargeable batteries, batteries or direct A/C power supply that is internal with or external of the unit.

Figure 10:
FIG. 10 is an example of a graphical user interface or GUI appropriate for a treatment strategy page in certain embodiments of the invention.

In further embodiments, the delivery platform 1 may be controlled by means of a user interface that operates to receive user input communicated to an electronic control unit 5 through an input/output (I/O) device (10 in FIG. 10 for example).

A user interface is any device for rendering information to, or requesting information from a user and includes at least one of textual, graphical, audio, visual, animation, and/or haptic elements.

The I/O device(s) (FIG. 1, 10) appropriate for this invention includes any sensory orient input and/or output device, such as an audio, visual, haptic, olfactory, and/or taste-oriented device, including, for example, a monitor, display, joystick, gamepad, overhead display, keyboard, keypad, mouse, trackball, joystick, gamepad, wheel, touchpad, touch panel, pointing device, stylus, microphone, speaker, video camera, camera, scanner, printer, haptic device, vibrator, tactile simulator, and/or tactile pad, footpad, strain gauge, motion sensor, pressure sensor, ocular sensor, horn, buzzer, piezoelectric transducer, optical fiber, Liquid Crystal Display (LCD), Light Emitting Diode (LED), organic polymer display, electric paper, cooler and/heater, external landmarks or features, potentially including a hardware interface or port to which such a device may be connected.

The control unit 5 may comprise a programmable logic controller (PLC) including a solid-state, microprocessor-based system used, via a network, to automatically monitor the status of field-connected sensor inputs, and automatically control communicatively-coupled devices of a controlled system (e.g., actuators, solenoids, relays, switches, motor starters, variable frequency drives, silicon-controlled rectifiers, pilot lights, ignitors, speakers, tape drives, printers, monitors, displays, etc. according to a user-created set of values and user-created logic and/or instructions stored in memory). The sensor inputs reflect measurements and/or status information related to the controlled system. The electronic control unit is designed to provide any of: automated input/output control; switching; counting; arithmetic operations; complex data manipulations; logic; timing; sequencing; communication; data manipulation; report generation; control; relay control; motion control; process control; distributed control; and/or monitoring processes, equipment, and/or other automation of the controlled system.

The control unit 5 may be programmed using ladder logic or some form of structured programming language specified in International Electrotechnical Commission (IEC) standard 61131-3 9 [3], namely, FBD (Function Block Diagram), LD (Ladder Design), ST (Structured Text), IL (Instruction List); and/or SFC (Sequential Function Chart).

In a more specific embodiment of the invention, a force sensor or strain gauge 210 is used to determine an internal characteristic such as a force or internal pressure generated during an injection process. This characteristic is then used as a control parameter by control unit 5 which generates corresponding commands to the electrical motor circuit 240 for the desired actuation of the plunger 220. The characteristic is used to calculate an exit pressure at which fluid ejected by the platform device 1 flows through the elongated tube 120. The motor assembly 200 is then operated in such a manner that the exit pressure or liquid flow rate is maintained at a predetermined level to insure that a patient does not suffer pain and/or tissue damage.

Figure 6:
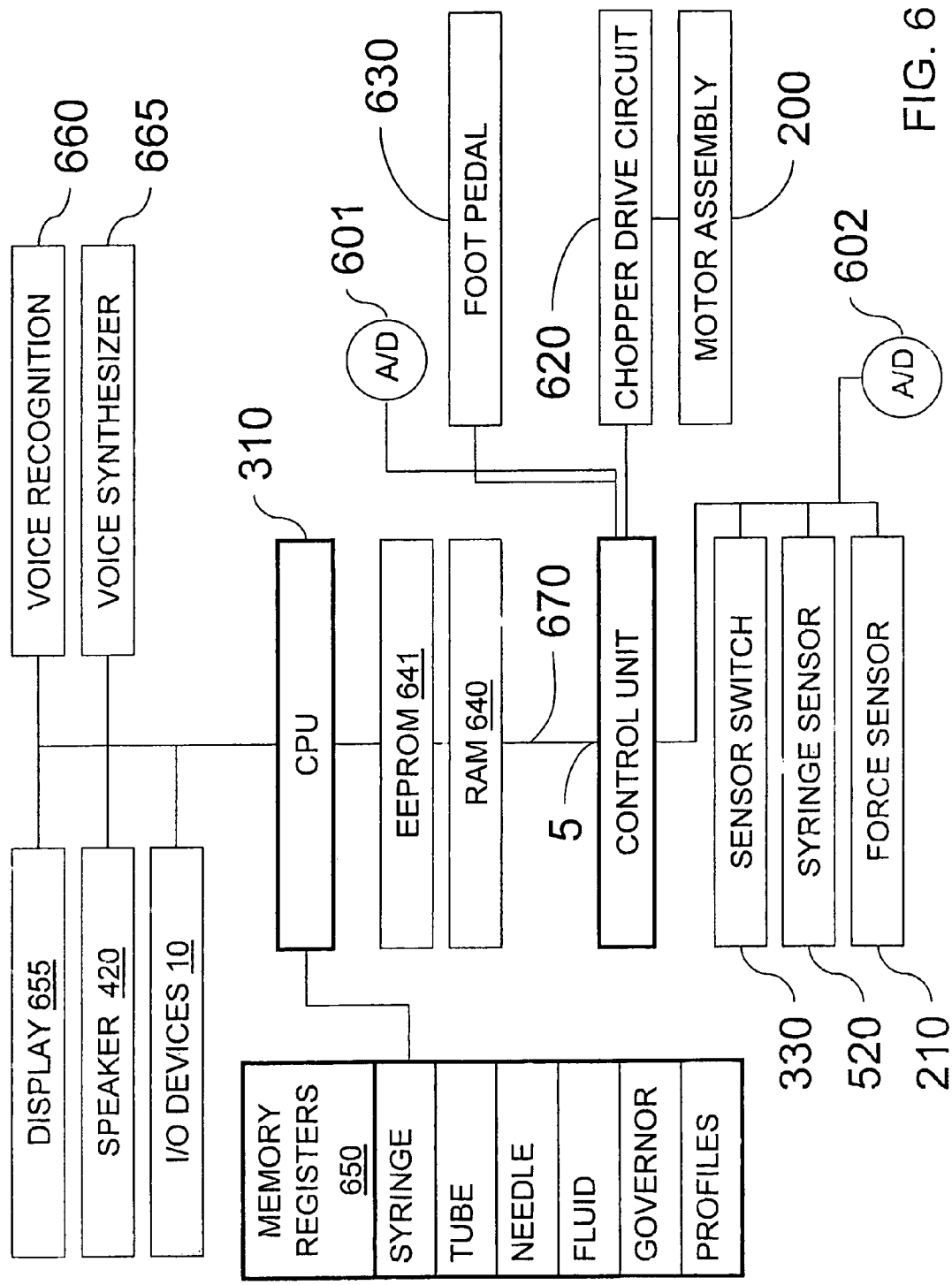
FIG. 6 is a schematic diagram of a further embodiment of the self-administration injection device of the invention.
Figure 7:
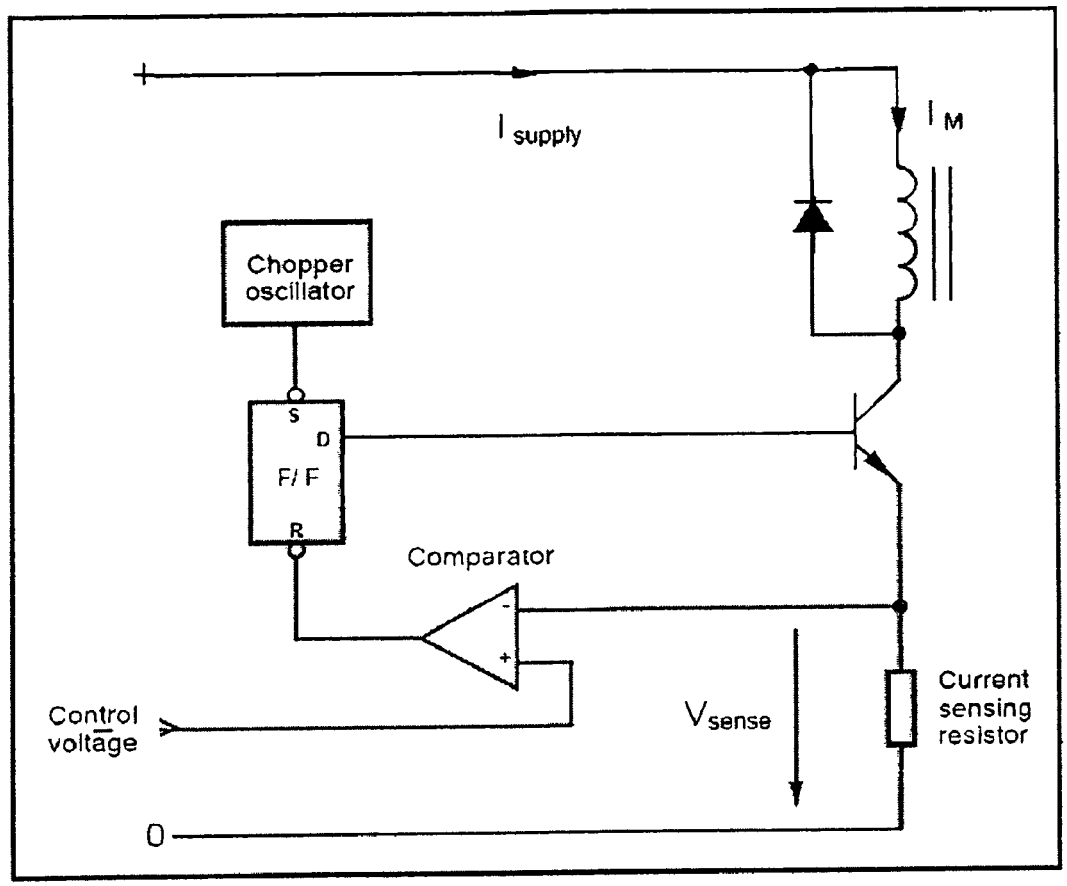
FIG. 7 is schematic diagram of a chopper drive circuit used for controlling a motor assembly in an embodiment of the invention.

FIG. 6 illustrates a specific embodiment of the integration of the control unit 5 with the various components of the delivery platform 1. The processor 310 is associated with the force sensor 210 through an A/D converter 602, a RAM chip(s) 640, an EEPROM 641, thermal coupling sensor in unit 520, and the limit switch 330. Using information derived from these elements, whose functions are described in more detail below, and in response to commands from the processor 310, the control unit 5 controls the operation of the motor assembly 200. More specifically the control unit 5 operates a chopper drive circuit 620 as, for instance, shown in FIG. 7, which generates stepping pulses to the motor assembly (FIG. 6, 200) to cause assembly 200 to turn in one of two directions by a discrete angular increment. The frequency of these pulses determines the speed of the motor. Separate speeds may be used for high flow rate, low flow rate purge, aspiration or charging. Referring back to FIG. 6, the system or the user (depending on the mode of operation) selects the values for all these speed parameters and the processor 310 then calculates the corresponding motor 200 speed (i.e. step frequency) using the dimensions of the syringe and the fluid delivery system.

Memory registers 650 are used to store programming and data for the use of the processor 310. More specifically, the memory registers 650 store six or more data banks, each dedicated to the following information: (a) syringes; (b) tubing; (c) needles; (d) fluids; (e) governor parameters; and (f) profiles consisting of a plurality of parameters for a particular procedure to be performed, customizable to each user. Each of these parameters is used to determine the control signals generated for the control unit 5. Each of these data banks contains the appropriate parameters for various commercially available products, or alternatively, parameter data derived using a specific algorithm. Information regarding the various elements for a particular configuration is entered through input devices 10 and is confirmed on the display device 655. These input devices may include a keyboard, a touch screen, a mouse, as well as a microphone. If a microphone is included, voice commands are interpreted by a voice recognition circuit 660.

The display device 665 is further used to provide an indication as well as instructions on the operation of the delivery system 1. The commands for the operation of motor assembly 200 are generated by the processor 310 and transmitted to a user interface I/O Device 10. The processor 310 is further in communication with the speaker 420 used to provide various audible messages, including spoken, pre-recorded or synthesized words, (generated by a voice synthesized circuit or software 665), chimes (e.g. at I/O devices 10), and so on, to provide instructions to the user and to provide other information about the current status of the whole system 1 and its elements without the need for the user having to rely solely on one means of user interface 10. The control unit 5 receives these commands through connection means and interface 670.

Also associated with the control unit 5 is a foot switch or pedal 630, comprising an air chamber with a flexible side wall, the side wall being arranged to change the volume of air and pressure within said chamber in response to activation by a human operator, i.e. the user or subject of the self-administrated injection. A pressure sensor (not shown) is part of the foot pedal and is arranged to provide information about the pressure to the control unit 5 via a corresponding A/D converter 601.

Figure 8:
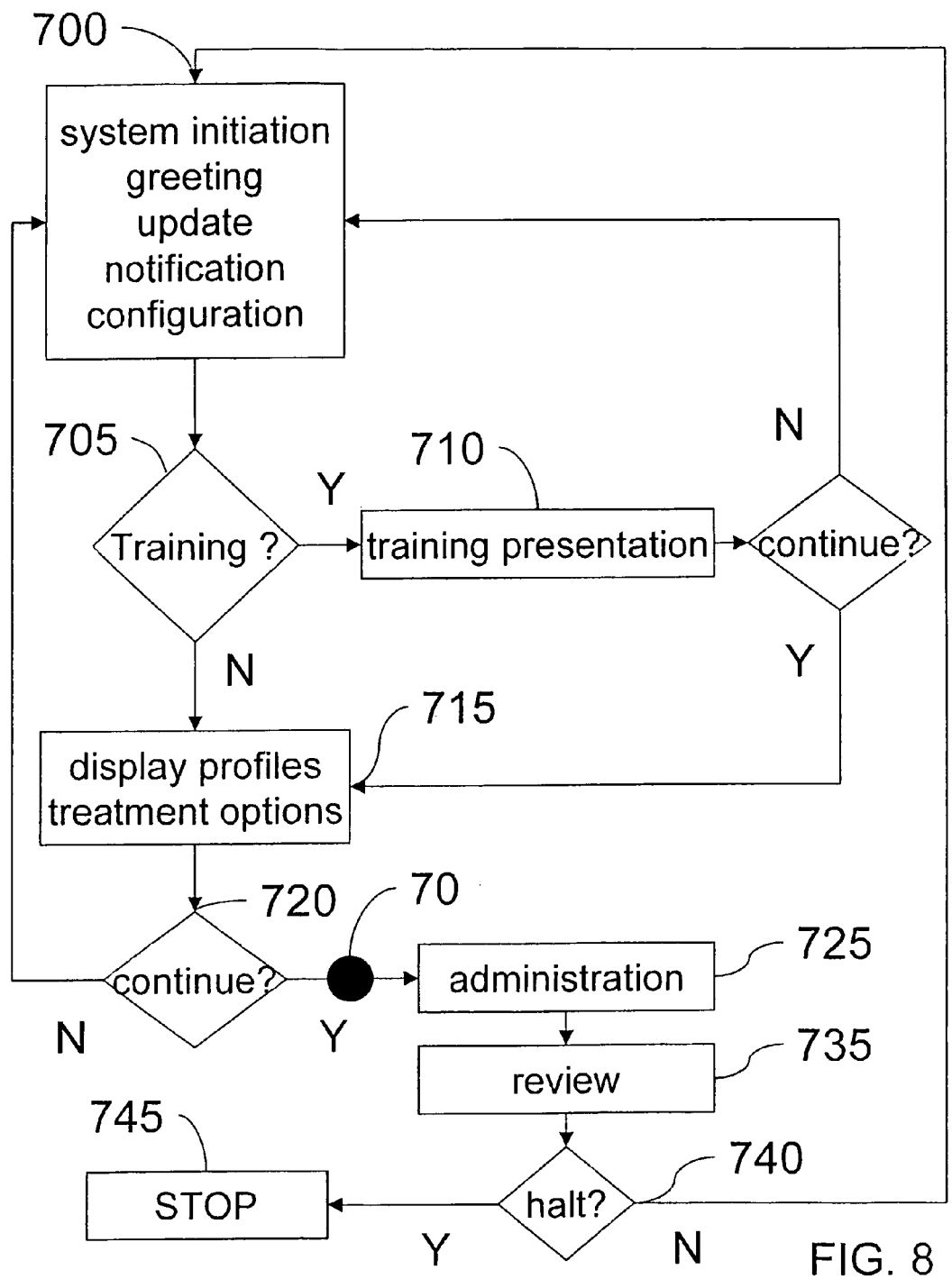
FIG. 8 is a flow chart of the sequence of operations of the self-administration injection device or platform of the invention.

The sequence of operation for the delivery platform 1 is now described in conjunction with FIG. 8. Starting in step 700, the system initialized and begins to exchange information with the user through an interface (FIG. 1 at 10; FIG. 5 at 410), from remote sources accessed through various I/O devices (FIG. 1 at 10; FIG. 5 at 410); through various sensors (FIG. 1, 20; FIG. 5, 210) as, for instance, a bar code scanner; and/or from internal data stores resident in memory (FIG. 5, 300; FIG. 6, 650) as facilitated by the processor (FIGS. 5 and 6, 310).

Step 700 involves, first, populating the memory registers (FIG. 6, 650) with the necessary information: type of syringe (FIG. 5, 110) being used, type (i.e. size and length) of tube (FIG. 5, 120), type of needle (FIG. 5, 130) being used, and name or other identification of the fluid or drug in the syringe (FIG. 5, 500). This information may be entered manually by the user or by a programmer of the unit before a first use via an I/O device (FIG. 1, 10) such as a keyboard or a touch screen disposed in the screen (FIG. 5, 390). Alternatively, a plurality of the corresponding items (for example, syringes) may be retrieved and presented to the user as a menu driven graphical user interface (GUI) with variable parameters to be selected by user input means (FIG. 1, 10). Alternatively the variable parameters may be selected via voice command. During step 700 user medical data; health care instructions; software updates, etc. can be uploaded and/or downloaded via alternate hardware interface means (FIG. 5, 410 and 430). The status of the system updates can be visually presented or be run in the background.

Figure 9:
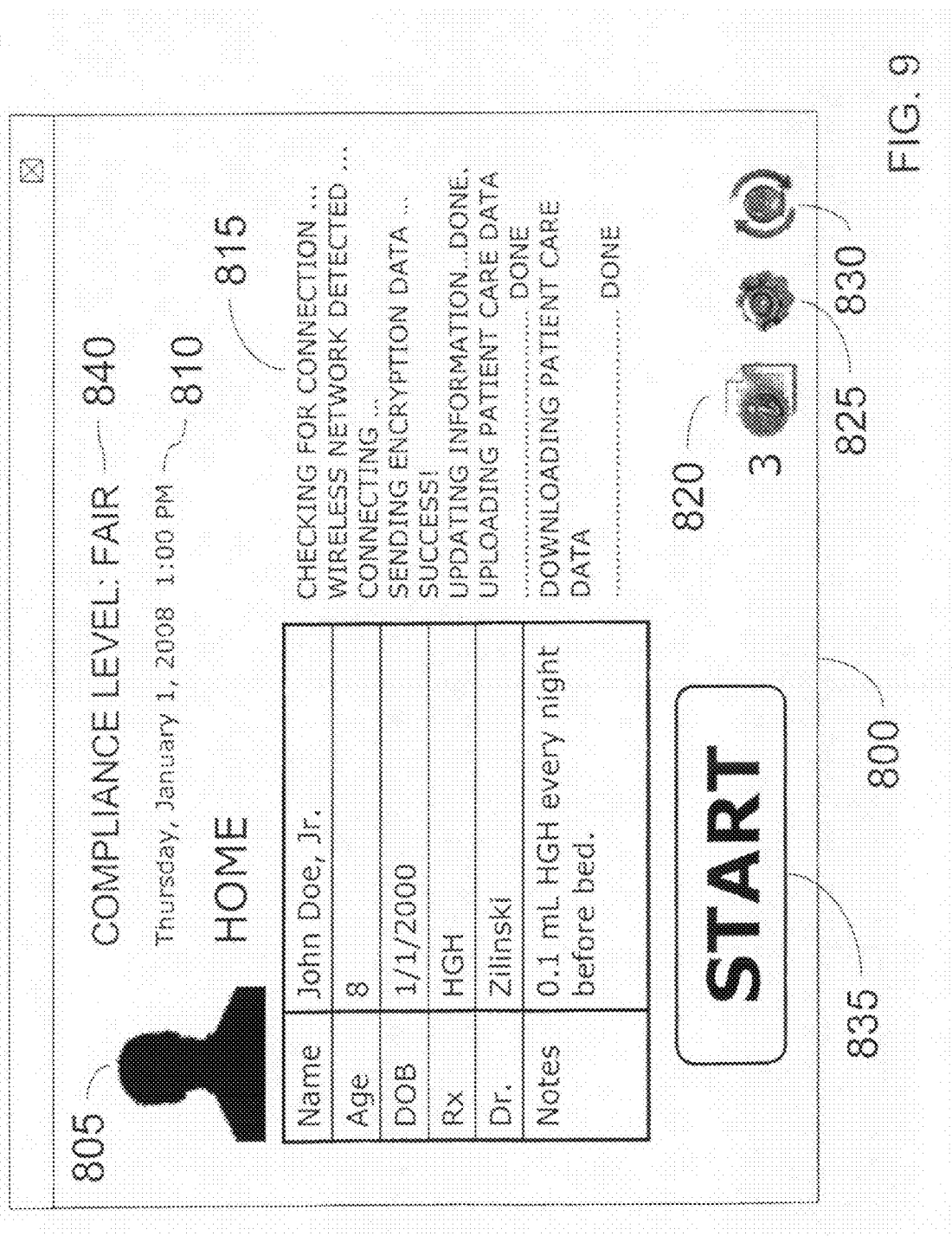
FIG. 9 is an example of a graphical user interface (GUI) appropriate for a home page in certain embodiments of the invention.

FIG. 9 is an example of one possible embodiment of the GUI for a touch-screen interface (FIG. 5, 390) presented to the user during step 700 of FIG. 8. After system initialization, corporate logo splash screen and greeting (not shown), the user is presented with a profile display home page 800. The screen displays the user's personal information 805; the current date and time 810; a system status area 815 for displaying the progress of any ongoing system processes; a reminder/message section 820 indicating if there are any pending messages, alerts, etc. and how many; a configuration icon 825 linking the user to a page to configure the variable parameters of the system 1; a system status icon 830 indicating the current status of the system (i.e. networking, loading, failure, warning, mode, etc.) and, a start button 835 to be touched when the user is ready to proceed with the administration of medicament. Also indicated on the home page 800 is an indicator of the medicament regimen compliance level 840 for the given user based on a review of the user's medical history contrasted with the prescribed regimen. This could be delineated with words (i.e., Good, Fair, Poor); graphics (number of stars); bars (level indicators); etc. This allows for a quick overview of the user's compliance for the benefit of the user as well as for the benefit of the caregiver and/or guardian to help ensure compliance.

Returning once more to FIG. 8, in step 705 system 1 will determine if it is configured so as to provide instruction before administration. If the system is configured to provide training it will begin making its training presentation step 710 before either continuing with review of treatment step 715 or returning to step 700. After the user has had a chance to review his or her treatment history, consider the delivery system's treatment recommendations, and make adjustments to various administration parameters (discussed in more detail below), the user is presented with the option 720 of continuing with the administration step 725 or returning to step 700. Before the system 1 will allow the user to proceed to the administration step 725, however, the system 1 will perform various failsafe checks 70 to determine whether it is safe to proceed (discussed in more detail below). Once the administration step 725 is allowed, the user, holding the handpiece 100 like a pencil, will insert the needle (FIG. 5, 130) into the tissue of the site that had been selected (explained in connection with FIG. 11 below and, e.g., the left arm), and the user presses down on the foot pedal (FIG. 6, 630) to self-administer the injection.

After the administration step 725 the system will next go to its review step 735 where it will update the system 1 and request feedback from the user as to his or her experience during the administration step 725. It will also review any relevant trends in the medical data (i.e., improved or worsened compliance history; errors noted during the administration of medicament; reminders to replenish medicament inventories, etc.). The system 1 will then determine 740 by various input means whether the user wishes to return to step 700 or to terminate the system process 745.

FIG. 10 is an example of one possible embodiment of the GUI for a touch-screen interface (FIG. 5, 390) presented to the user during step 715 of FIG. 8. During this step, the user is given a treatment strategy screen 900 from which he or she may select from a menu comprising: the user's sensitivity profile 901 (discussed in more detail below); the user's injection data record 905 (discussed in more detail below); and a review of the system's 1 treatment options 910. Next to the menu of options is an information window 915 that further guides the user in his or her selection process. The options profile also includes a link to a help routine 920 as well as the same notice 820 and configuration 825 links of the home page 800. This screen also has a link 925 to home page 800 and another link 930 that allows the user to proceed to the administration step 725.

Figure 11:
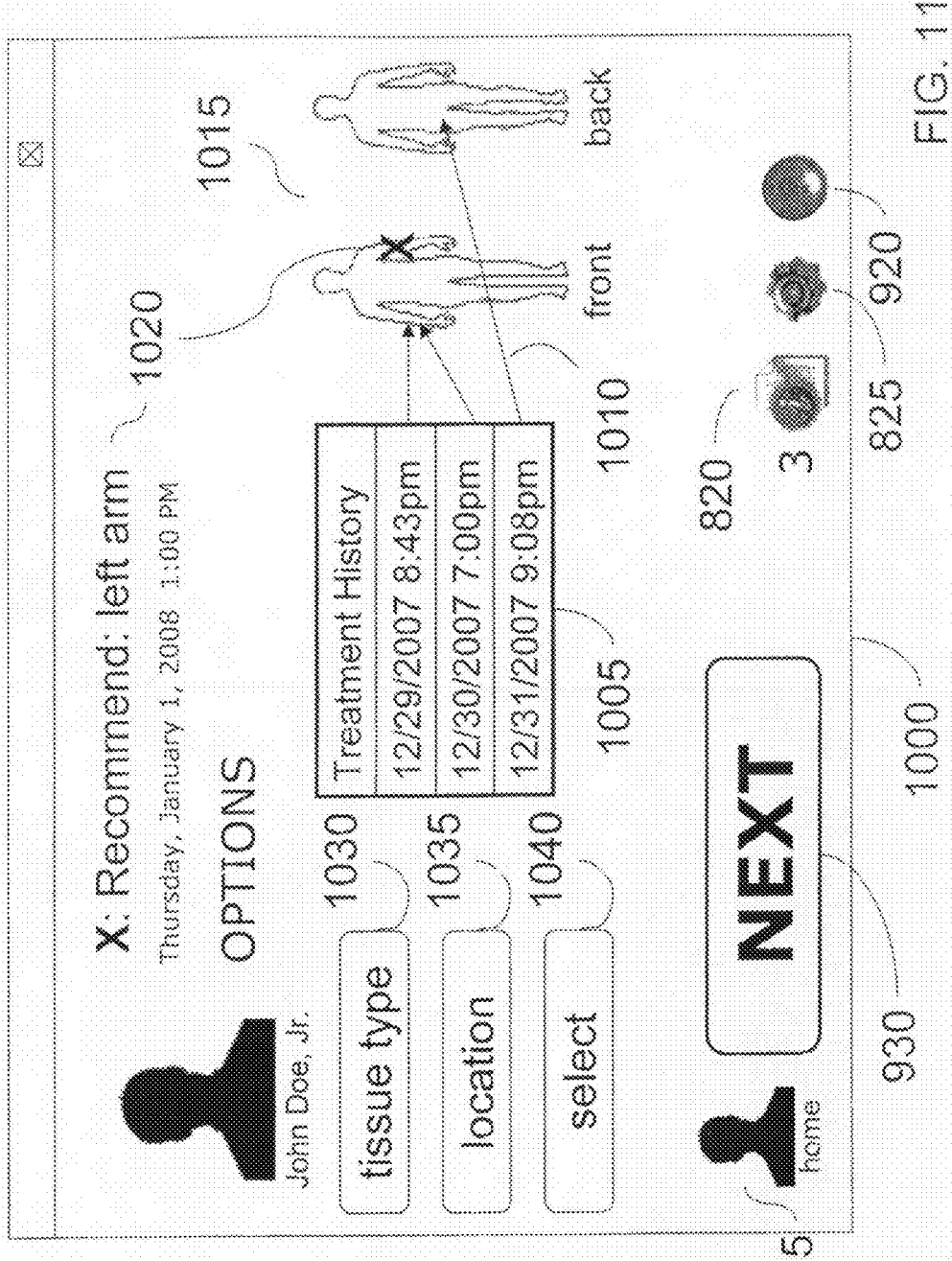
FIG. 11 is an example of a graphical user interface or GUI appropriate for a treatment options page in certain embodiments of the invention.

FIG. 11 is an example of one possible embodiment of the GUI for a touch-screen interface (FIG. 5, 390) presented to the user during step 715 of FIG. 8 should the user select the treatment options menu item 910.

Selecting the treatment options menu item 910 will present the user with a treatment options screen 1000. On this screen, the user will be presented with his or her treatment history 1005 which are indicated via arrows 1010 on a graphic representation of the front and half profiles of a human FIG. 1015. The system's default recommendation 1020 is generated from an analysis of the user sensitivity profile 901, the injection data record 905, the system configuration 825 and the drug protocols in memory (FIG. 6, 650; FIG. 5, 300) and displayed prominently on the screen 1000. The user is free to make adjustment to the injection site location by selecting an appropriate tissue type 1030 and location of administration 1035. After adjusting parameters 1030 and 1035 the user can finalize the adjustments by pressing the select 1040 menu item. Once all of the necessary adjustments have been made, the patient has the option of continuing to the administration step 725 or returning to the home page 800.

The configuration of the system 1 can be performed locally through interface means (FIG. 1, 10 and FIG. 5, 390, 400, 410, 430) or remotely through various communication means. When doing so the user selects the type of operation required (i.e., injection) the high and low flow rates, and the optimal pressure limit. This last parameter is very important because it controls the amount of pain and tissue damage that the patent may suffer during the procedure. Additional parameters may also be selected in this area, such as charge flow rates, aspiration volume and flow rate, purge volume and flow rate and so on. A layer of abstraction is imposed on the configuration of the system 1 through the use of the user sensitivity profile 901 which allows the user to make multiple, automatic adjustments to the system 1 based on the average parameters preferred by members of a particular category (i.e. highly sensitive, relatively sensitive, non sensitive).

In one embodiment of the invention, the system, and more particularly the processor (FIGS. 5 and 6, 310) then uses these parameters to determine an appropriate administration profile describing the sequence and programming characteristics required to deliver the fluid through the needle at the requested, or optimized rate. The profile for each particular syringe-tube-needle combination is calculated and stored into the memory (FIG. 6, 650) earlier. These profiles have unique characteristic for each type of procedure.

Alternatively, the processor (FIGS. 5 and 6, 310) may be programmed to perform the calculations necessary to generate the profiles.

Returning again to FIG. 8, after the failsafe component 70 releases the system 1 to begin the administration step 725 the administration of the medicament begins with the user administering the medicament on a selected site on the body as previously determined during the treatment options step 715. The injection process may be fully automated at this point or the user can choose to control the speed of the injection with I/O means (FIG. 1, 10, FIG. 5 400; FIG. 6, 630).

Referring back to FIG. 5, the processor 310 keeps track of the position of the plunger 220 counting the steps taken by motor assembly 200. Alternatively, or in addition, other sensor switches 210 may also be provided to detect and confirm the location of the plunger 220.

The motor assembly 200 is preferably made with rare earth permanent magnets so that it can be relatively compact and yet generate a large torque.

Figure 12:
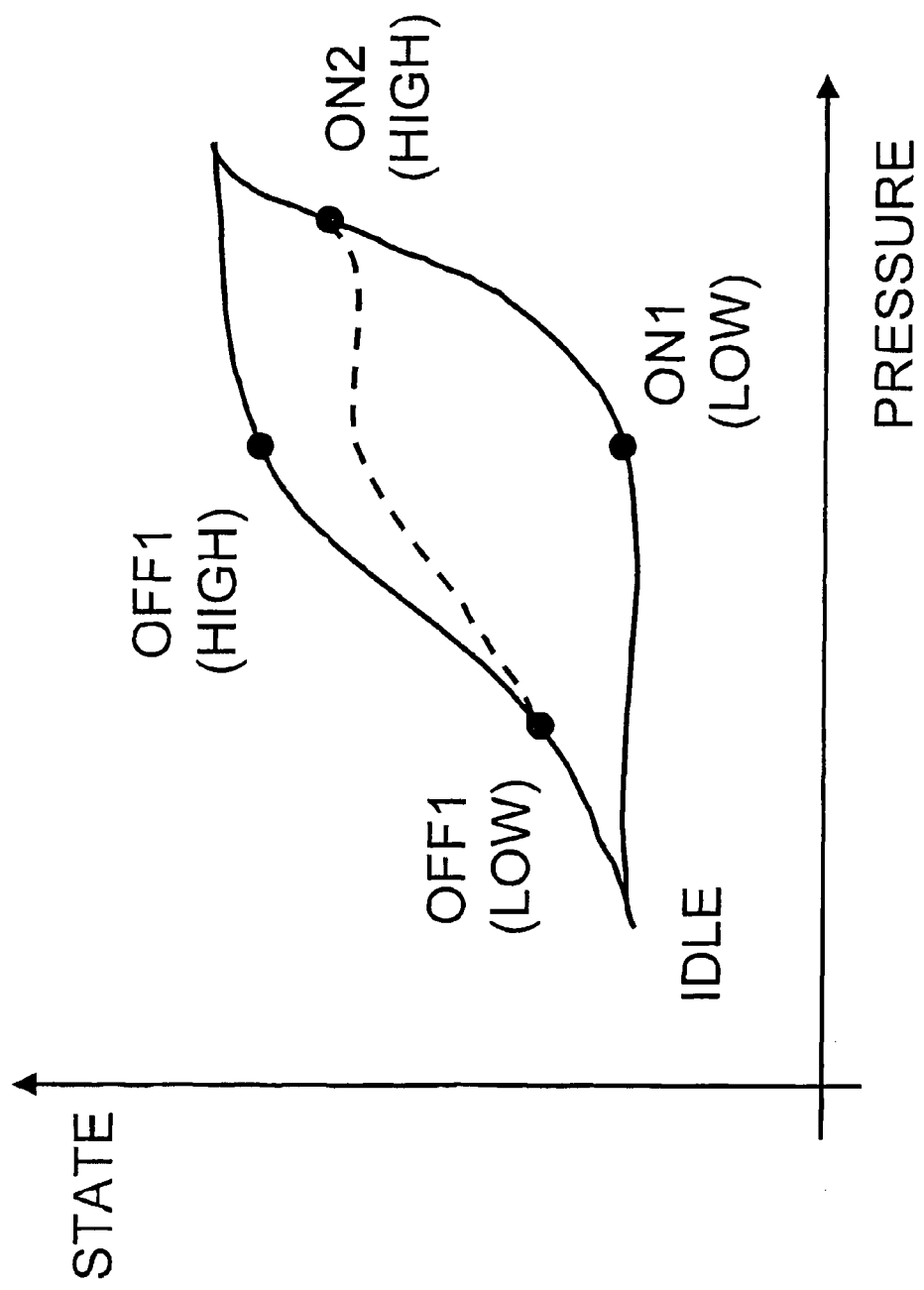
FIG. 12 is a graph plotting pressure against the state of control signals derived from a foot pedal of the system of the invention.

As mentioned above and referring to FIG. 6, a control means, such as a foot pedal 630 includes an air bellows and an air pressure sensor (not shown). The output of the air pressure sensor is fed to the A/D converter 601 and the digital equivalent of the foot switch output is fed to the control unit 5. The control unit 5 uses the foot pedal mounted sensor in conjunction with a look-up table stored in the EEPROM 641 to determine or generate a switch indication signal indicative of the position of the switch. It has been found that, for best response and sensitivity, the position of switch is translated into four different positions or states using hysterisis. In other words, as indicated in FIG. 12, initially the switch is in an idle state. As the switch is depressed, its internal pressure increases. When it reaches a first value ON1, the control unit 5 generates a LOW FLOW command. If the pressure increases but does not exceed a level ON2 then, the LOW FLOW command is maintained. If the pressure is reduced to below a level OFF1, then the idle state is indicated. Typically the pressure OFF1 is lower than ON1. If the pressure exceeds ON2 then a HIGH FLOW command is generated. This HIGH FLOW command is not turned off until the pressure drops below a pressure level OFF2 that is lower than ON2. If a LOW FLOW command is received, then the drug is dispensed at a low rate. If a HIGH FLOW command is received, the drug is dispensed at a high flow rate. The actual values for HIGH and LOW FLOWS have been previously set as discussed above.

The current pressure indicated by force sensor (FIG. 5, 210) is checked against a threshold which is the peak pressure that is safe for the system. This pressure level depends on the components selected for the system and is calculated by the failsafe component 70 of the system 1. In addition, the exit pressure level is also monitored. As discussed above, it has been found that the fluid pressure during an injection plays a very important role in the amount of pain and tissue damage that a patient feels during an injection. At low levels of pressure, the pain is minimal so that the patient is almost comfortable. However, if the pressure increases beyond a certain level, the injection becomes very painful. Therefore an important consideration in the present invention is the control of the flow rate in a manner that ensures a low exit pressure level. The optimal levels can be averaged out and categorized as user sensitivity profiles (FIG. 11, 901) which can be further customized by the user during the treatment options step (FIG. 8, 715).

If either pressure (i.e., the pressure within the system or the exit pressure) is found to be excessive, the control unit (FIGS. 5 and 6, 5) instructs the motor assembly (FIG. 5, 200) to reduce the flow rate.

The flow rate and various other parameters are relayed to the user by various output means (FIG. 1, 10; FIG. 6, 655) so that he should be able to see very easily what is happening. Whenever an abnormal pressure is detected, a visual as well as an audible alarm is provided.

When the designated volume has been reached or if a stop command is issued by the user the administration step (FIG. 8, 725) terminates. At this point, the forward motion of the syringe plunger (FIG. 5, 220) stops, and a message is displayed for the user to withdraw the needle.

Continuing, while referring to FIG. 5, the motor assembly 200 is reversed and runs in the opposite direction for a predetermined time causing the plunger 220 to retract. After the plunger 220 is moved the predetermined distance, it is stopped. The plunger 220 is then moved forward again until it is returned to its original position. The motor assembly 200 is then stopped.

At this point, and reference once more to FIG. 8, the system 1 performs the review step 735 the details of which are discussed in detail above. The user, once having completed step 735, is then able to stop the system 745 return to step 700 and the home page 800. The failsafe component 70 will prevent an unsafe repetition of the process unless it is specially overridden as discussed in more detail below.

The system has been described so far as performing an injection process. However, it is obvious to one skilled in the art that it can be used just as effectively to perform a biopsy, for instance to perform a spinal tap, or other similar anaerobic procedures. Essentially the same parameters can be used for this process, with some minor modifications. For instance, instead of defining an exit pressure, the clinician now defines an entry pressure. Some of the subroutines, such as purging, charging or aspiration are not required for biopsy at all.

Example 2

Figure 13:
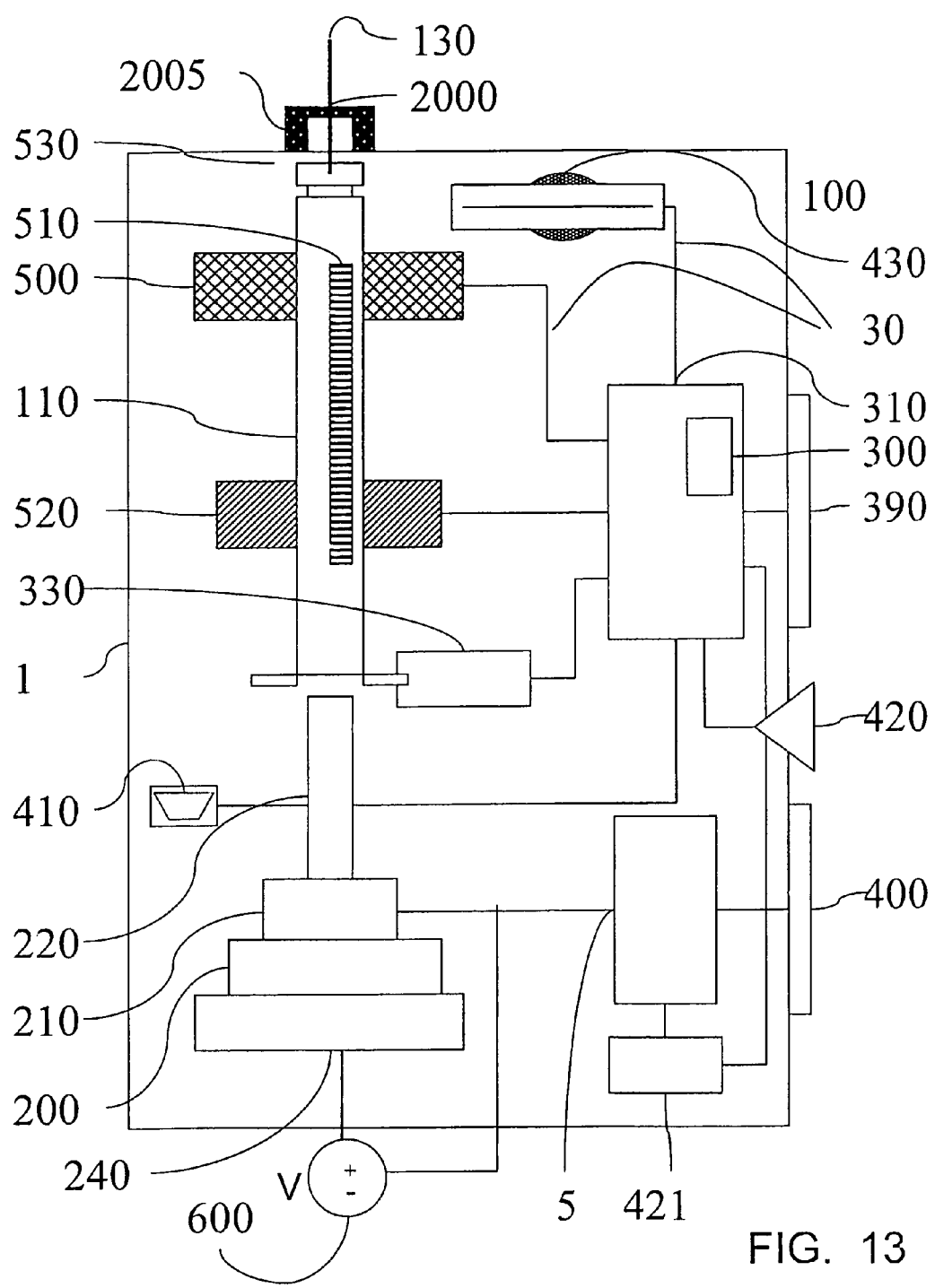
FIG. 13 is a schematic plan view of a self-administration injection device in accordance with a still further embodiment of the invention.

Turning now to FIG. 13, an alternate single unit embodiment of the delivery platform 1 is illustrated. Unlike the multiple unit embodiment of example 1, the delivery platform 1 does not require a handpiece assembly (FIG. 5, 100, 120), rather a disposable needle 130 is attached directly to the syringe 110 and the medicament (not shown), with the syringe 110 designed to be secured by an adaptor 2000 mounted on the platform 1, and the needle 130 secured by a threaded needle hub 2005. Example 2 retains the remaining elements of example 1, including the ability for the user to control the rate and flow of the medicament and therefore the exit pressure by a control activator unit (FIG. 13, 400) such as a foot pedal (FIG. 6, 630).

Training Component

Various embodiments of the invention comprise a training component (FIG. 1, 60) that is designed to overcome the initial fear and apprehension of at-home self-injection commonly observed when using other technologies. Patient phobias stem primarily from a basic lack of familiarity with the proper technique to perform a self-injection. To stem this fear, lack of familiarity is overcome by embodiments of this invention that provide interactive teaching before, during and after the actual injection while using the injection device. The training component (FIG. 1, 60) is comprised of teaching modes that are verbal, visual and haptic instructions on how to perform a safe and comfortable injection using a system that controls many of the more dangerous elements of self-injection. These instructions can be provided on an interactive basis during the self-injection process. The instructions can be verbal instructions, as well as digital-video animations or movies. In various embodiments a touch screen LCD screen (FIG. 5, 390; FIG. 6, 655) would be provided to input commands as well as display information such as digital video to be displayed for teaching and training purposes. Teaching steps would be contextual to the action being performed and contemporaneous therewith. In other embodiments, the teaching steps may be reviewed before performing any action with the medicament delivery platform. The user may select from a variety of teaching modes and formats. Teaching modes could include user levels of sophistication as, for example, a beginner level (with in-depth discussion of the procedures to be followed during the regimen), a novice level (providing abbreviated guidance); or an expert level (providing instructional cautions alone). Alternatively, the teaching component may be configured to be in a silent mode so as to provide no commands or feedback at all.

Verbal instructions can be generated in the form of predetermined electronic signals associated with human speech generated by an onboard processor (FIG. 5, 310; FIG. 6, 665). In various embodiments, such speech could constitute recorded verbal instructions digitalized in various audio codecs known in the art as, for instance, MPEG Audio Layer-3 (MP3) and waveform (.wav) sound formats.

In some embodiments, generated audio codecs are sent as electronic signals from a processor (FIG. 5, 310) to an audible output device as, for instance, a microspeaker (FIGS. 5 and 6, 420); in other embodiments an electronic signal is sent from a processor to a voice synthesizer microprocessor (FIG. 6, 665), both of which are commercially available as digital or analog circuits, or combinations of the same. In other embodiments, the audio signal can be sent to external resources such as attached speakers and similar peripheral devices (FIG. 5, 410).

Visual instructions can be generated in the form of predetermined electronic signals associated with digitalized images and video streams in the form of known image codecs as, for instance, Joint Photographic Experts Group (JPEG) format and in the form of known video codecs as, for instance, Moving Picture Experts Group (MPEG) format.

Another possible embodiment of the training component would be to utilize a microphone (FIG. 6, 660) or similar recording device in order to record speech and other signals which an on-board processor can convert into digital instructions as communicated to the system by the subject. The microphone may be integral with the system or peripheral to it.

In various embodiments of the invention, visual instructions may be generated as electronic signals by an onboard processor (FIG. 5, 310) and relayed to a Light Emitting Diode (LED) device or a Liquid-Crystal-Display (FIG. 5, 390) both of which are known in the art.

In one possible scenario, a subject begins using the training component by turning the medicament delivery platform on. Upon initialization, an LCD screen or similar display device, either integrated with the medicament delivery system or peripheral to it, will begin playing a video clip of the next step showing the subject how to properly attached the set up the delivery platform to begin administrating a particular drug. The unit could also provide verbal instructions to "coach" the user through each step of the process, simultaneously displaying the proper technique on the display. When the delivery platform detects that it is ready to begin administration of the medicament, the subject will be instructed in the proper use of the injection device so that it administers the medication to the subject with the least, possible discomfort and physical trauma. In some embodiments of the invention, the training component will ask the user interactive questions such as: "Where do you wish to perform today's injection?", simultaneously displaying, for instance, various profiles of a human figure with appropriate areas to be selected by touch (see FIG. 11, 1015), or by presenting a list of appropriate areas of the body to be selected by touch (FIG. 11, 1035). Alternatively, the question(s) could be answered verbally, recorded by an onboard or peripheral microphone (FIG. 6, 660) and processed into digital instructions. A combination of the above described methods of receiving input from the subject is also possible.

The training component (FIG. 1, 60) can made recommendations to the subject based on prior data collected and stored in electronic memory. For instance, the training component may interact with the drug monitoring and reporting component (FIG. 1, 71, described in detail below) and determine that a previous injection was received in the subject's abdominal area. In response, the training component (FIG. 1, 60) may send an audio signal (with a possible simultaneous visual display of audio or video) stating "Your last injection was received in your abdomen. Would you like to selected a different site for today's injection?". To which the subject can respond by providing feedback audibly or tactilely, or in a combination of any of the methods described above. These responses could be logged and reported to the drug monitoring and reporting component (FIG. 1, 71) for storage and subsequent retrieval, as for instance, in the form of an injection data record for the event.

When administering the injection, the training component FIG. 1, 60 could describe to the subject what they might be feeling while simultaneously informing the subject of how long the procedure is estimated to last and providing verbal comfort. This would correspond to the coaching step 80 of FIGS. 2-4 that occurs during the medicament administration phase (step 725 of FIG. 8).

After the procedure is completed the training component FIG. 1, 60 could provide verbal encouragement and post-treatment recommendations (FIG. 8, step 735). It could also request feedback of the experience from the patient that it could then use to modify various parameters of the administration procedures and tailor subsequent recommendations to the user. If the patent reports adverse affects from the administration of medicaments, this can be immediately reported to a physician or emergency operator by way of the drug monitoring and reporting component (FIG. 1, 71).

In another possible scenario, the training component FIG. 1, 60 could explain each step of the injection process including the setup of the injection device; purging and preparation prior to the injection; the injection event; post-operative care of injection site; and unit breakdown post-procedure.

In yet a further example of the training component FIG. 1, 60, after initializing the medicament delivery platform FIG. 1, 1, the training component can begin presenting a tutorial on how to prepare a particular drug for administration—in this case, one that must be refrigerated and warmed to an optimal temperature before injection. The training component may be integrated with the failsafe component (FIG. 1, 70, described in more detail below), such failsafe component receiving data from a temperature sensor or sensors (FIGS. 5 and 6, 520) located in the device injection cradle and from a separate temperature sensor or sensors (FIGS. 5 and 6, 520) for determining the ambient room temperature. The failsafe component (FIGS. 1 and 8, 70) is able to process the temperature data and relay information back to the training component (FIG. 1, 60) as to whether the optimal temperature for injecting the medicament has been attained. Upon receiving confirmation from the failsafe component (FIGS. 1 and 8, 70) the training component may proceed with the instruction to administer the medicament.

Failsafe Component

Various embodiments of the invention comprise a failsafe component (FIGS. 1 and 8, 70) which is designed to provide critical failsafe check points at certain stages of the treatment regimen.

In one embodiment of the invention, the failsafe component (FIG. 1 and 8, 70) prevents the introduction of counterfeit and/or adulterated and/or expired drugs that could be illegally introduced into the supply chain. Unique identification (FIGS. 5 and 13, 510) of drugs can determined using encryption labeling and/or proprietary markings on the drug and/or drug container that will verify authenticity of the drug at the time of at-home self-administration. Other possible identifying features include: manufacturer identification, lot and/or serial numbers and critical details of the medication which can be identified, recorded and transferred for verification and future tracking by way of a remotely integrated database tracking system accessed through the drug monitoring and reporting component. Other embodiments of this invention may utilize a unique bar code or IR identification tag, radio-frequency identification (RFID) tags and transponders, spectrographic analysis and comparisons against known drug spectrum fingerprints, magnetic readers and optical scanners. In yet another embodiment, the delivery platform could be designed to only accept drug vessel with unique physical features of a propriety design. All of the above described devices and techniques may be used alone or in combination as possible means by which to confirm the identity, purity and quality of any medicament introduced into the delivery platform.

One embodiment of the failsafe component (FIGS. 1 and 8, 70) includes means by which a user may be warned about possible drug overdose, negative drug interactions and potential allergic reaction to medicaments that are loaded into the delivery platform. Acceptable dosages and times for administration can be calculated based on information stored and received from the drug monitoring and reporting component.

In another example, the correct drug dosage and regimen may be electronically communicated to the medicament delivery system (FIG. 1, 1) by a health care provider by way of the drug monitoring and reporting component (FIG. 1, 71). When a medicament is loaded into the delivery platform (FIG. 1, 1), means for identifying the substance would be initiated and the information obtained would be cross-referenced with an internal or remotely accessed database to be confirmed for administration to the user. The amount and type of medication, together with a time-date stamp and user identification is gathered by the failsafe component (FIG. 1, 70) and compared with the drug monitoring and reporting component ((FIG. 1, 80) (i.e. cross-referenced with the user profile, past medical history, drug interaction data, and the injection data record) to confirm the that the correct drug, dosage and regimen is being applied to the subject before application.

As a further example of the failsafe component (FIGS. 1 and 8, 70) of the present invention, the user may be identified by various identification means known in the art as, for instance, the entry of a username and password through an LCD touchscreen interface (FIGS. 1 and 6, 10; FIG. 5, 390); or voice (FIG. 6, 660) and/or fingerprint recognition software processing data from a variety of input means known in the art. This would prevent the accidental use or misuse of the medicament delivery system by unauthorized third parties.

In the event that the failsafe component (FIGS. 1 and 8, 70) determines that it is not safe to proceed, it can relay a message to the user through integrated or peripheral audio and video devices (FIGS. 1 and 6, 10). Further, the failsafe component could lock-down the drug delivery system (FIG. 1, 1) until the matter can be further investigated by the user or appropriate third-parties and agencies. Reactivation may be accomplished by sending electronic instructions to do so via the drug monitoring and reporting component (FIG. 1, 71). Alternatively, or in addition to remote electronic reactivation, would be the ability to reactive the medicament delivery component locally by various input means known in the art. Still further, any lock-down protocol may be overridden by the user by means of indicating approval (either verbally or tactilely) after having received adequate audio and visual warnings and disclaimers.

Drug Monitoring and Reporting Component

Various embodiments of the invention comprise a drug monitoring and reporting component (FIG. 1, 71) which is designed as a means for storing, sending and receiving relevant medical information to facilitate a safe and effective treatment regimen for the end user.

The drug monitoring and reporting component i (FIG. 1, 71) is itself comprised of one or more of the following subcomponents: user medical profile, the injection data record, user sensitivity profile and user physiological parameter profile. The drug monitoring and reporting component is also comprised of means for communication with other components within the medicament delivery system (FIG. 1, 1) and with remote systems.

Embodiments of the user medical profile would include medical and identification information relevant to the to a particular subject. For example, the user profile could include the subject's medical history in standardized machine interpretable data (structured messages, standardized content), also know as electronic health and medical records (EHRs/EMRs), that are treated as Individually Identifiable Health Information (45CFR164.501) under the Health Insurance Portability and Accountability Act (HIPAA), US Code of Federal Regulations, Title45, Volume 1 (Revised Oct. 1, 2005) in the United States and In the European Union (EU), several Directives of the European Parliament and of the Council [4]. Embodiments of the drug monitoring and reporting component (FIG. 1, 71) would comply with all applicable ERM and ERH transmittal, storage, control and accountability standards, including: ASTM International Continuity of Care Record; ANSI X12 (EDI); CEN—CONTSYS (EN 13940); CEN—EHRcom (EN 13606); CEN—HISA (EN 12967); DICOM; HL7—HL7 messages; HL7 Clinical Document Architecture (CDA) documents; ISO—ISO TC 215; and openEHR as well as standards set by CCHIT—Certification Commission for Healthcare Information Technology [5].

Elements describing the injection data records are described above and incorporated by way of reference herein. The information stored in the injection data record will include, but is not limited to: unique identifiers of the medicament, volume of medicament administered, time and date of administration, medicament flow-rate and exit pressure, site of application, delivery platform unit identification, environment measurements (ambient temperature, drug temperature, etc.) and system logs (status, warnings, errors, failures, etc.).

Embodiments of the user sensitivity profile could include means to allow the user to store customized settings on the medicament delivery platform (FIG. 1, 1) to adopt an individuals pain perception needs thereby adapting to each individual's perceived pain threshold tolerances. These settings are obtained from the compliance assistance component (FIG. 1, 72) which is described in more detail below. Such settings can be recalled automatically upon system initialization to calibrate the delivery platform (FIG. 1, 1) to the user's requirements and may also be reviewed by third parties, such as health care providers and technicians, in the event of a post-procedure negative patient outcome.

The drug monitoring and reporting component (FIG. 1, 71) may be further characterized as having a user physiological parameter profile which is used in conjunction with the dynamic diagnostic drug delivery component (FIG. 1, 73, described below) to auto-adjust the setting of the medicament delivery platform (FIG. 1, 1) in such respects as (by way example) the volume of the drug administered and the speed by which it administered. The physiological parameter profile may also be configured to receive data on relevant physiological parameters of the patient obtained through measurement means and to provide the stored data to the dynamic diagnostic drug delivery component (FIG. 1, 73) to calibrate a drug regimen appropriate to the current condition of the subject.

By way of example, the user physiological parameter profile may collect blood-glucose levels from a diabetic subject who must self-test for blood-levels on a daily basis. By means of a third-party blood-glucose measuring device, the level of blood-glucose can be determined by the subject and, in turn, entered into the user physiological parameter profile by a variety of input means as discussed above. This data is stored in the drug monitoring and reporting component (FIG. 1, 71) until it is accessed by the dynamic diagnostic drug delivery component (FIG. 1, 73) of the invention which will adjust the amount of insulin to be administered to a subject on that particular occasion. These adjustments will be tempered to be within acceptable ranges by the feedback loop from the failsafe component (FIGS. 1 and 8, 70) as described above. This information also becomes part of the digital data record that is stored within the drug monitoring and reporting component (FIG. 1, 71) to be recalled in the future by both the user, treating physicians and other, authorized third parties.

In various embodiments, the drug monitoring and reporting component (FIG. 1, 71) is operative to receive a "smart card" for accessing portable EHRs and EMRs as described in detail above. The "smart card" may be interfaced with the delivery platform (FIG. 1, 1) at a digital media slot (FIGS. 5 and 13, 430).

Compliance Assistance Component

Various embodiments of the invention comprise a compliance assistance component (FIG. 1, 72), designed to facilitate a subject's compliance with a prescribed drug regimen.

The compliance assistance component (FIG. 1, 73) is itself comprised of one or more of the following subcomponents: a calendar/clock/alarm feature, means to generate a user specific injection profile, means to generate a user sensitivity profile.

The calendar/clock/alarm feature integrated with the drug monitoring and reporting (FIG. 1, 71) and failsafe components (FIGS. 1 and 8, 70) to track the subjects injection data records and compare such records with the subject's user profile to be able to remind that subject of the next injection event and provide an easy way to review compliance (FIG. 9, 840) for both the subject and relevant third parties, such as health care providers.

In some embodiments of the compliance assistance component (FIG. 1, 72) use information gathered from the drug monitoring and reporting component (FIG. 1, 71) to project near term medication needs and determine whether adequate amounts of a medicament are readily available to the subject or whether more should be ordered. A further embodiment could notify the subject of his or her current drug inventory and provide notice if more medication should be ordered in order to prevent a lapse in treatment. A further embodiment would also encompass means by which the compliance assistance component (FIG. 1, 72) could contact necessary third parties (such as health care providers and pharmacies through the drug monitoring and reporting component FIG. 1, 71) that a new prescription must be filled, by type and quantity of medicament and by what date.

The user will enter the treatment strategy page (FIG. 10, 900) and select the "User Sensitivity Profile" menu item (FIG. 10, 901) from the main menu or sub-menu. A series of questions will be answered by the user. Based on the answers to these questions the unit will offer an appropriate injection setting for the subcutaneous injection. Example of the questions: A) Would you say that you are sensitivity to load sounds? B) Would you agree that you are sensitivity to cold rooms? C) Would you agree that you find loud noises irritating? Questions would be designed to elicit the person's subjective sensitivity level to simulations. The delivery system (FIG. 1, 1) would then select an appropriate Sensitivity User Setting. It may either decrease the flow-rate and/or exit-pressure at which the injection is performed to a new pre-defined level or it may increase the flow-rate and/or exit/pressure to a new pre-defined level.

The user may select from amongst the "User Sensitivity Profile Settings": Examples: a) Highly Sensitivity: This setting would slow the flow-rate and/or reduce exit-pressure by a certain percentage for all injection performed; b) Normal Sensitivity: This setting would use standard setting for all injections; c) Stoic Sensitivity: This setting would speed up all flow-rate and/or increase exit-pressure setting by a certain percentage for all injections performed.

Dynamic Diagnostic Drug Delivery Component

The dynamic diagnostic drug delivery component (FIG. 1, 73) allows for real time analysis of the user's physiological condition as a factor in determining the appropriate course of treatment for each treatment event. The diagnostic component (FIG. 1, 73) is operative to receive data from outside of the delivery system (FIG. 1, 1) which it can then use to adjust various administration parameters such as dosage—which would correlate with flow rates and the run time of the motor assembly (FIGS. 5 and 13, 200). The calculations to adjust administration parameters in response to such external physiological data would be performed by the processor (FIGS. 5, 6 and 13, 310). Examples of appropriate algorithms for calculating the dosage requirements are well known in the art and include, for example, the INTELLIGENT DOSING SYSTEM (™) (IDS) (Dimensional Dosing Systems, Inc., Wexford, Pa.) a software suite that incorporates patient-specific, dose-response data in a mathematical model and then calculates the new dose of the medication needed to achieve the next desired therapeutic goal [6].

Injection and Drug Type Perameters

Below are examples of the parameters that are unique to an injection site or to a drug type, according to the present invention.

The term "injection parameter" is used here to identify a setting for an injection that is different for different tissue types and thus which the device of the invention uses based on the users selection of the site for the self-injection.

| | | SITE SPECIFIC INJECTION PARAMETERS | | | | |
|---|---|---|---|---|---|---|
| Site Specific Tissue Type | Drug Type | Patient Preference Setting | Dispos. Comb. Config Type | Maximum Exit Pressure | Flow Rate cc/sec | Volume |
| Abdomen | Insulin | Normal | Type-1 | 500 mm/Hg | 0.01 | 0.8 ml |
| Abdomen | Growth Hormone | Stoic | Type-2 | 500 mm/Hg | 0.015 | 0.6 ml |
| Abdomen | Fertility | Sensitive | Type-1 | 300 mm/Hg | 0.02 | 1.4 ml |
| Thigh | Insulin | Normal | Type-1 | 850 mm/Hg | 0.04 | 0.8 ml |
| Thigh | Growth Hormone | Normal | Type-3 | 850 mm/Hg | 0.02 | 0.6 ml |
| Deltoid | Insulin | Sensitive | Type-2 | 1200 mm/Hg | 0.03 | 0.8 ml |
| Deltoid | Growth Hormone | Sensitive | Type-1 | 1200 mm/Hg | 0.02 | 0.4 ml |
| Fore Arm | Insulin | Stoic | Type-2 | 1000 mm/Hg | 0.02 | 0.8 ml |
| Fore Arm | Growth Hormone | Normal | Type-2 | 1000 mm/Hg | 0.08 | 1.2 ml |
| Buttocks | Insulin | Normal | Type-1 | 1800 mm/Hg | 0.02 | 1.2 ml |
| Buttocks | Growth Hormone | Sensitive | Type-1 | 1800 mm/Hg | 0.04 | 1.2 ml |
| Buttocks | Fertility | Normal | Type-2 | 1800 mm/Hg | 0.04 | 1.8 ml |

| Drug Type: Parameters | | | |
|---|---|---|---|
| Drug: | Viscosity | Temperature | Spec Wt. lbs/cubic in |
| Insulin | $3 \cdot 4^{-7}$ | 72° F. | 0.03250 |
| Human Growth Hormone | $1 \cdot 9^{-7}$ | 65° F. | 0.03611 |
| Fertility Drugs | $1 \cdot 8^{-7}$ | 72° F. | 0.03561 |
| Monoclonal Antibody | $2 \cdot 2^{-7}$ | 55° F. | 0.03321 |

| Disposable Component Parameters | | | | | | | |
|---|---|---|---|---|---|---|---|
| Disposable Combination Config. Type | Cart. Size volume | Cart. Width ml | Cart. Length cm | Tubing Diameter I.D. | Tubing Length inch | Needle gauge diam. | Needle Length inch |
| Type-1 | 1.8 ml | 0.5 | 5.04 | 0.030 | 50 | 30 | ½ |
| Type-2 | 0.8 ml | 0.4 | 2.54 | 0.020 | 40 | 32 | ½ |
| Type-3 | 2.0 ml | 0.6 | 7.20 | 0.040 | 30 | 27 | 1 |

Site Specific Injection Parameters are unique to this invention. It is defined as those parameters that are necessary to create a unique combination of injection variables when performing a site specific injection that is be controlled by exit-pressure and/or rate for that specific tissue site. The first parameter to define is the Site Specific Tissue Type, examples provided are Abdomen, Fore Arm, Thigh, Deltoid and Buttocks. Each of these tissues is composed of a different tissue density owing to the type of tissue this anatomic location is composed from. The Abdomen region is predominately loose connective tissue beneath the dermis. This tissue has a low density or high tissue compliance in comparison to Deltoid. The Deltoid region is composed predominately of muscle tissue which has a high density tissue type with low compliance. Therefore, each of the tissues that have been identified to have a unique tissue type density or tissue compliance. Drug delivery into these tissues create a resistance to the flow of a drug into these tissues that can be quantified for an exit-pressure of a fluid entering these tissues at a specific rate.

Previous experimentation by the inventor has demonstrated that tissue type will produce an exit-pressure value for a specific rate for a given anatomic site for drug injection.

Site Specific Injection Parameters are the variables noted in the chart provided above. The variables include; Site Specific Tissue Type, Drug Type, Patient Preference Setting, Disposable Combination Configuration Type, Maximum Exit-Pressure, Flow-rate, Drug Volume. Changes in any one of these variables will produce a different clinical outcome for the patient. For this invention these variables are defined prior to the use of the injection system. These variables are stored in the database of the instrument and can be updated in the event new applications or new medications or new tissue injection site parameters or new instructions for use of the device are defined in the future, using the up-loading means of the invention such as the wire or wireless link to the Internet that the platform of the invention is capable of.

Settings of the Site Specific Injection Parameters can be understood by the following examples: Site Specific Tissue Type; Abdomen could have setting of Maximum Exit-pressure of 500 mm/Hg at a flow-rate of 0.01 cc/sec. The viscosity of the drug as well as the temperature of the drug used with these settings would affect the patient experience. In addition, the specific disposable configuration would also effect the injection experience, therefore it is important to quantify the size of cartridge, cartridge width, cartridge length, tubing length, tubing I.D., needle gauge and needle length.

Selecting a different Site Specific Injection Tissue Type location would require variables to be changed to compensate for the different variables. Specifically tissue type density would require a different exit-pressure and/or flow-rate to provide a successful injection experience. Additionally if any of the other parameters of the Drug or Disposable Component Parameters, these two could affect the outcome of the injection experience. It is therefore critical that these parameters be defined and stored within the database of the injection system.

It is also understood that the Site Specific Injection Parameter would include a Patient Preference Setting that would globally change the settings to make the injection more comfortable for the patient. There are 3 settings noted; Normal, Stoic & Sensitive. The normal setting would utilize the Maximum Exit-Pressure and/or Flow-rate programmed. The "Stoic" setting would increase the "Maximum Exit-pressure and/or Flow-rate" by specified percentage. An example is 5% in this discussion. This would increase the flow-rate and maximum exit-pressure used during the injection. The "Sensitive" setting would decrease the Maximum Exit-Pressure and/or Flow-rate by a specified percentage. An example is 7% in this discussion. The flow-rate and maximum exit-pressure would be reduced by 7% from the programmed values making the injection slower and performed with a lower maximum exit-pressure.

While specific embodiments of the invention have been shown and described in detail to illustrate the application of the principles of the invention, it will be understood that the invention may be embodied otherwise without departing from such principles.

Regardless of the content of any portion (e.g., title, field, background, summary, abstract, drawing figure, attachment, etc.) of this application, unless clearly specified to the contrary, such as via an explicit definition, assertion, or argument, with respect to any claim, whether of this application and/or any claim of any claiming priority hereto, and whether originally presented otherwise: there is no requirement for the inclusion of any particular described or illustrated characteristic, function, activity or element, any particular sequence of activities, or any particular interrelationship of elements; any element can be integrated, segregated and/or duplicated; any activity can be repeated, performed by multiple entities, and/or performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all sub-ranges therein.

Any information in any material that has been incorporated by reference herein, is only incorporated by reference to the extent that no conflict exists between such information and the other statements and drawings set forth herein. In the event of such conflict, including a conflict that would render invalid any claims seeking priority hereto, then any such conflicting information in such incorporated by reference material is specifically not incorporated by reference herein.

Accordingly, the descriptions and drawings are to be regarded as illustrative in nature, and not as restrictive.

REFERENCES

[1] Pear, Robert. 1999. Group Asking U.S. for New Vigilance in Patient Safety. New York Times, November 30.
[2] Syringe History . . . A History Of The Development Of Syringes. http://www.diabetesexplained.com/syringe-history.html (Accessed Jan. 9, 2008).
[3] IEC—Publications found with ICS code: (English). http://www.iec.ch/cgi-bin/procgi.pl/www/iecwww.p?wwwlang=e&wwwprog=sea002-27.p&prog_db=db1&ics=35.240.50 (Accessed Jan. 15, 2008).
[4] European Parliament and Council (24 Oct. 1995): EU Directive 95/46/EC—The Data Protection Directive.
[5] Electronic medical record—Wikipedia, the free encyclopedia. http:H/en.wikipedia.org/wiki/Electronic_medical_record (Accessed Jan. 10, 2008).
[6] Cook, Curtiss B et al. 2005. The Intelligent Dosing System: application for insulin therapy and diabetes management. Diabetes technology & therapeutics 7, no. 1:58-71.

What is claimed is:

1. A self-administration injection apparatus for allowing a user to inject a fluid medicament into a selected tissue of the user at a level of at least one injection parameter that the user finds comfortable and can set for an injection process, the apparatus comprising:
   a platform;
   a fluid medicament containing cartridge carrying unique identification information about the medicament, the cartridge being disposable and detachably connected to the platform;
   a cartridge holder capable of accepting the fluid medicament containing cartridge and being connected to the platform;
   a handpiece with tubing connected to at least one of the cartridge and cartridge holder, and a needle connected to the tubing, the handpiece being held by the user for manual insertion of the needle into a selected tissue of the user at any one of a plurality of injection sites, the tissue at each injection site being associated with at least one injection parameter that is different for each injection site;

an identification reader connected to the platform for reading the unique identification information of the medicament containing cartridge;

a drive unit in the platform for driving fluid medicament from the cartridge, through the tubing and the needle, and into a selected tissue of the user at the one of the injection sites selected by the user, during the injection process, and at the injection parameter that is associated with the selected tissue at the injection site that is selected by the user;

a drive unit control for controlling the drive unit to drive medicament from the cartridge at the injection parameter;

a central processing unit connected to the identification reader for cooperating with the identification reader to obtain information regarding at least one of the medicament in the cartridge and the injection parameter, based on the unique identification information of the cartridge, the central processing unit being connected to the drive unit control for performing the injection process at one of the injection parameters corresponding to the injection site selected by the user;

a memory connected to the central processing unit for storing a plurality of the different injection parameters associated with tissues at the plurality of injection sites for the user;

information output means connected to the central processing unit for providing information to the user about the injection process;

operation input means connected to the central processing unit and being operated by the user to selecting the injection site for the injection process and for controlling initiation of the injection process, the central processing unit responding to a user selection of one of the injection sites to control the injection process to proceed at the injection parameter for the associated tissue at the selected injection site;

up-loading means for up-loading and for storing additional information including at least one of injection parameters, medicament information, general information and instructions to said central processing unit and memory, of additional information and additional injection profiles with different injection parameters associated with tissues at the plurality of injection sites; and the central processing unit being programmed to perform a training session to determine from the user, a user-selected level of at least one of the injection parameters that the user finds comfortable for an injection process into the selected tissue, and for storing the level in the memory, the central processing unit causing each injection process to be performed at not greater than the level of the at least one of the injection parameters that the user finds comfortable.

2. The apparatus of claim 1, including an injection schedule calendar stored in the memory, a clock for determining a current time, and reminder means programmed into the central processing unit for reminding the user when a next injection process is due by activation of the information output means.

3. The apparatus of claim 1, including a sensor for sensing at least one injection parameter for each injection process, an injection schedule calendar stored in the memory, a clock for determining a current time, reminder means programmed into the central processing unit for reminding the user when a next injection process is due by activation of the information output means, the central processing unit including data recording means for recording a time when each injection process is performed and the injection parameter for each injection process and creating injection data for each injection and for storing the injection data in the memory.

4. The apparatus of claim 1, including medical history information about the user stored in the memory, a sensor for sensing the at least one injection parameter for each injection process including an amount of medicament injected, an injection schedule calendar stored in the memory, a clock for determining a current time, reminder means programmed into the central processing unit for reminding the user when a next injection process is due by activation of the information output means, the central processing unit including data recording means for recording a time when each injection process is performed and the injection parameter for each injection process including the amount of medicament injected, and creating injection data for each injection and for storing the injection data in the memory, the apparatus including communication means for communicating the injection data from the apparatus so that a medical practitioner for the user can access the injection information.

5. The apparatus of claim 1, wherein the information output means includes a visual display for providing the user with a visual indication of each injection site to facilitate a user selection of the selected injection site for an injection process and other information related to the injection process.

6. The apparatus of claim 1, wherein the information output means includes auditory information for providing the user information related to the injection process.

7. The apparatus of claim 1, including user profile data concerning a level of at least one of the injection parameters that the user finds comfortable for an injection process, stored in the memory, the central processing unit causing each injection process to be performed at not greater than the level of the at least one of the injection parameters that the user finds comfortable.

8. The apparatus of claim 1, wherein the central processing unit is programmed to perform one or more of the training sessions to determine from the user, a use-selected level of at least one of the injection parameters that the user finds comfortable for an injection process for each of the tissues, and for storing the levels in the memory, the central processing unit causing each injection process to be performed at not greater than the user-selected level of the at least one of the injection parameters that the user finds comfortable for each tissue.

9. The apparatus of claim 1, wherein the central processing unit is programmed so that the at least one injection parameter that is set to the user-selected level that the user finds comfortable during the training session, is changeable to a different level by the user using the operation input means during an injection process to further improve the user's comfort.

10. The apparatus of claim 1, wherein the central processing unit is programmed so that at least one of the injection parameters is changeable to a different level by the user using the operation input means during an injection process to further improve the user's comfort.

11. The apparatus of claim 1, wherein the at least one injection parameter that is set to the user-selected level that the user finds comfortable during the training session, is at least one of pressure and flow rate of the fluid medicament during the injection process.

12. The apparatus of claim 1, wherein the central processing unit is programmed so that the at least one injection parameter that is set to the user-selected level that the user finds comfortable during the training session or another one of the injection parameters is changeable to a different user-selected level by the user using the operation input means during an injection process to further improve the user's comfort, the at least one injection parameter that is set to the user-selected level or that is changes during the injection process being at least one of pressure and flow rate of the fluid medicament during the injection process.

13. A self-administration injection apparatus for allowing a user to inject a fluid medicament into a selected tissue of the user at a level of at least one injection parameter that the user finds comfortable and can set for an injection process, the apparatus comprising:

a platform;

a fluid medicament containing cartridge that is disposable and is detachably connected to the platform;

a cartridge holder capable of accepting the fluid medicament containing cartridge and being connected to the platform;

a handpiece with tubing connected to at least one of the cartridge and cartridge holder, and a needle connected to the tubing, the handpiece being held by the user for manual insertion of the needle into a selected tissue of the user at any one of a plurality of injection sites, the tissue at each injection site being associated with at least one injection parameter that is different for each injection site;

a drive unit in the platform for driving fluid medicament from the cartridge, through the tubing and the needle, and into a selected tissue of the user at the one of the injection sites selected by the user, during the injection process, and at the injection parameter that is associated with the selected tissue at the injection site that is selected by the user;

a drive unit control for controlling the drive unit to drive medicament from the cartridge at the injection parameter;

a central processing unit connected to the drive unit for control performing of the injection process at one of the injection parameters corresponding to the injection site selected by the user;

a memory connected to the central processing unit for storing a plurality of the different injection parameters associated with tissues at the plurality of injection sites for the user; and operation input means connected to the central processing unit and being operated by the user to selecting the injection site for the injection process and for controlling initiation of the injection process, the central processing unit responding to a user selection of one of the injection sites to control the injection process to proceed at the injection parameter for the associated tissue at the selected injection site;

the central processing unit being programmed to perform a training session to determine from the user, a user-selected level of at least one of the injection parameters that the user finds comfortable for an injection process into the selected tissue, and for storing the level in the memory, the central processing unit causing each injection process to be performed at not greater than the level of the at least one of the injection parameters that the user finds comfortable.

14. The apparatus of claim 13, wherein the central processing unit is programmed so that the at least one injection parameter that is set to the user-selected level that the user finds comfortable during the training session, is changeable to a different level by the user using the operation input means during an injection process to further improve the user's comfort.

15. The apparatus of claim 13, wherein the central processing unit is programmed so that at least one of the injection parameters is changeable to a different level by the user using the operation input means during an injection process to further improve the user's comfort.

16. The apparatus of claim 13, wherein the at least one injection parameter that is set to the user-selected level that the user finds comfortable during the training session, is at least one of pressure and flow rate of the fluid medicament during the injection process.

17. The apparatus of claim 13, wherein the central processing unit is programmed so that the at least one injection parameter that is set to the user-selected level that the user finds comfortable during the training session or another one of the injection parameters is changeable to a different user-selected level by the user using the operation input means during an injection process to further improve the user's comfort, the at least one injection parameter that is set to the user-selected level or that is changes during the injection process being at least one of pressure and flow rate of the fluid medicament during the injection process.

18. A self-administration injection apparatus used by an individual user on oneself in which parameters of the injection are defined contemporaneously with the injection by said user based on a subjective pain response of the user during said injection, the apparatus comprising:

a platform;

a fluid medicament containing cartridge that is disposable and is detachably connected to the platform;

a cartridge holder capable of accepting the fluid medicament containing cartridge and being connected to the platform;

a handpiece with tubing connected to at least one of the cartridge and cartridge holder, and a needle connected to the tubing, the handpiece being held by the user for manual insertion of the needle into a selected tissue of the user at any one of a plurality of injection sites, the tissue at each injection site being associated with at least one injection parameter that is different for each injection site;

a drive unit in the platform for driving fluid medicament from the cartridge, through the tubing and the needle, and into a selected tissue of the user at the one of the injection sites selected by the user, during the injection process, and at the injection parameter that is associated with the selected tissue at the injection site that is selected by the user;

a drive unit control for controlling the drive unit to drive medicament from the cartridge at the injection parameter;

a central processing unit connected to the drive unit for control performing of the injection process at one of the injection parameters corresponding to the injection site selected by the user;

a memory connected to the central processing unit for storing a plurality of the different injection parameters associated with tissues at the plurality of injection sites for the user; and operation input means connected to the central processing unit and being operated by the user to selecting the injection site for the injection process and for controlling initiation of the injection process, the central processing unit responding to a user selection of one of the injection sites to control the injection process to proceed at the injection parameter for the associated tissue at the selected injection site;

the central processing unit being programmed to perform a training session to determine from the user, a user-selected level of at least one of the injection parameters that the user finds comfortable for an injection process into the selected tissue, and for storing the level in the memory, the central processing unit causing each injection process to be performed at not greater than the level of the at least one of the injection parameters that the user finds comfortable.

* * * * *